(12) United States Patent
Nakamura et al.

(10) Patent No.: US 11,785,845 B2
(45) Date of Patent: Oct. 10, 2023

(54) COMPOSITION

(71) Applicants: FUJIFILM Corporation, Tokyo (JP); The University of Tokyo, Tokyo (JP)

(72) Inventors: Koki Nakamura, Kanagawa (JP); Hiroki Sugiura, Kanagawa (JP); Yukio Tani, Kanagawa (JP); Tetsuya Matsushita, Kanagawa (JP); Tetsuya Watanabe, Kanagawa (JP); Junichi Takeya, Tokyo (JP); Toshihiro Okamoto, Tokyo (JP)

(73) Assignees: FUJIFILM Corporation, Tokyo (JP); The University of Tokyo, Tokyo (JP)

( * ) Notice: Subject to any disclaimer, the term of this patent is extended or adjusted under 35 U.S.C. 154(b) by 86 days.

(21) Appl. No.: 17/503,449

(22) Filed: Oct. 18, 2021

(65) Prior Publication Data
US 2022/0045283 A1 Feb. 10, 2022

Related U.S. Application Data

(63) Continuation of application No. PCT/JP2020/017188, filed on Apr. 21, 2020.

(30) Foreign Application Priority Data

Apr. 24, 2019 (JP) .................................. 2019-082825

(51) Int. Cl.
*H01B 1/00* (2006.01)
*C09D 7/20* (2018.01)
(Continued)

(52) U.S. Cl.
CPC ....... *H10K 85/6572* (2023.02); *C07D 471/22* (2013.01); *C09D 5/24* (2013.01);
(Continued)

(58) Field of Classification Search
CPC . H01B 1/121; C09D 7/20; C09D 5/24; C07D 471/22
See application file for complete search history.

(56) References Cited

U.S. PATENT DOCUMENTS

2006/0284169 A1 12/2006 Park et al.
2011/0262828 A1 10/2011 Noda et al.
(Continued)

FOREIGN PATENT DOCUMENTS

BR 102013031176 A2 2/2016
JP 2006-351543 A 12/2006
(Continued)

OTHER PUBLICATIONS

International Search Report issued in PCT/JP2020/017188; dated Jul. 7, 2020.
(Continued)

*Primary Examiner* — Mark Kopec
(74) *Attorney, Agent, or Firm* — Studebaker & Brackett PC

(57) ABSTRACT

An object of the present invention is to provide a composition capable of manufacturing an organic thin film transistor having excellent carrier mobility even under low temperature conditions. The composition of the present invention contains a compound represented by Formula (1) and an alcohol represented by Formula (S1).

(Continued)

US 11,785,845 B2

Page 2

(1)

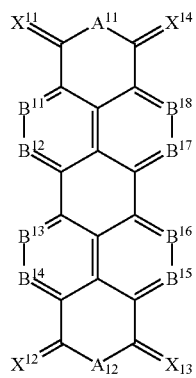

(S1)

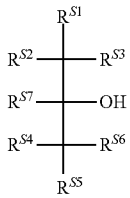

12 Claims, 4 Drawing Sheets

(51) Int. Cl.
*H10K 85/60* (2023.01)
*C07D 471/22* (2006.01)
*C09D 5/24* (2006.01)
*H01B 1/12* (2006.01)
*H10K 10/46* (2023.01)

(52) U.S. Cl.
CPC ............... *C09D 7/20* (2018.01); *H01B 1/121* (2013.01); *H10K 10/466* (2023.02)

(56) References Cited

U.S. PATENT DOCUMENTS

| 2013/0330231 | A1  | 12/2013 | Swager et al. |
| 2014/0273339 | A1* | 9/2014  | Seferos ............... H10K 85/621 |
|              |     |         | 528/8 |
| 2017/0018724 | A1  | 1/2017  | Tsuyama et al. |
| 2019/0131546 | A1  | 5/2019  | Fukuzaki et al. |
| 2019/0222219 | A1* | 7/2019  | Wen ...................... H03M 1/38 |

FOREIGN PATENT DOCUMENTS

| JP | 2009-152112 A  |   | 7/2009 |
| JP | 2015-195362 A  |   | 11/2015 |
| JP | 2018-006745 A  |   | 1/2018 |
| WO | 2009/082666 A1 |   | 7/2009 |
| WO | WO 200908266   | * | 7/2009 |
| WO | 2013/180801 A1 |   | 12/2013 |

OTHER PUBLICATIONS

International Preliminary Report on Patentability and Written Opinion issued in PCT/JP2020/017188; dated Sep. 28, 2021.
Sahnawaz Ahmed et al., "Solvent Directed Morphogenesis and Electrical Properties of a Peptide-Perylenediimide Conjugate", Langmuir, 2018, vol. 34, pp. 8355-8364.
Sarah Holliday et al., "Advances in Charge Carrier Mobilities of Semiconducting Polymers Used in Organic Transistors", Chemistry of Materials, 2014, 26, pp. 647-663.
An Office Action; "Notice of Reasons for Refusal," mailed by the Japanese Patent Office dated Nov. 1, 2022, which corresponds to Japanese Patent Application No. 2021-516134 and is related to U.S. Appl. No. 17/503,449; with English language translation.
Jiajun Wu et al., "Direct Synthesis of Large-Scale Ortho-Iodinated Perylene Diimides: Key Precursors for Functional Dyes," Organic Letters, vol. 19, No. 19, Sep. 28, 2017, pp. 5438-5441, American Chemical Society.
An Office Action; "Notice of Reasons for Refusal," mailed by the Japanese Patent Office dated Mar. 7, 2023, which corresponds to Japanese Patent Application No. 2021-516134 and is related to U.S. Appl. No. 17/503,449; with English language translation.

* cited by examiner

COMPOSITION

CROSS-REFERENCE TO RELATED APPLICATIONS

This application is a Continuation of PCT International Application No. PCT/JP2020/017188 filed on Apr. 21, 2020, which claims priority under 35 U.S.C. § 119(a) to Japanese Patent Application No. 2019-082825 filed on Apr. 24, 2019. The above application is hereby expressly incorporated by reference, in its entirety, into the present application.

BACKGROUND OF THE INVENTION

1. Field of the Invention

The present invention relates to a composition.

2. Description of the Related Art

Since it is possible to be made lighter, cheaper, and more flexible, to a device or the like, which uses a logic circuit including a field effect transistor (FET), radio frequency identifier (RFID; RF tag), and memory, which are used in liquid crystal displays and organic electric luminescence (EL) displays, the use of an organic thin film transistor (organic TFT) having an organic semiconductor film (organic semiconductor layer) has been studied.

As a compound for forming such an organic semiconductor film, JP2018-6745A discloses an organic semiconductor compound having an azaperylene skeleton.

SUMMARY OF THE INVENTION

The present inventors have found that there is room for improvement in manufacturing conditions in a case of manufacturing an organic thin film transistor using the compound having an azaperylene skeleton, which is disclosed in JP2018-6745A. For example, it has been required to be able to manufacture an organic thin film transistor having excellent carrier mobility at a lower temperature (for example, room temperature).

Therefore, an object of the present invention is to provide a composition capable of manufacturing an organic thin film transistor having excellent carrier mobility even under low temperature conditions.

As a result of intensive studies on the above-described objects, the present inventors have found that the above-described objects can be achieved by the following configurations, and have completed the present invention.

[1] A composition comprising:
a compound represented by Formula (1) described later; and
an alcohol represented by Formula (S1) described later.
[2] The composition according to [1],
in which, in Formula (1) described later, at least one of $B^{11}$, $B^{12}$, $B^{13}$, $B^{14}$, $B^{15}$, $B^{16}$, $B^{17}$, or $B^{18}$ is —N=.
[3] The composition according to [1] or [2], further comprising:
an organic solvent other than the alcohol represented by Formula (S1) described later. [4] The composition according to [3],
in which the organic solvent consists of only one or more atoms selected from the group consisting of a carbon atom, a hydrogen atom, and a halogen atom.
[5] The composition according to [3] or [4],
in which, in the composition, a content of the alcohol represented by Formula (S1) described later is 10% by volume or more with respect to a total content of the alcohol represented by Formula (S1) described later and the organic solvent.
[6] The composition according to any one of [1] to [5],
in which the alcohol represented by Formula (S1) described later in the composition is an alcohol represented by Formula (S2) described later.
[7] The composition according to any one of [1] to [6],
in which the alcohol represented by Formula (S1) described later in the composition is an alcohol represented by Formula (S3) described later.
[8] The composition according to any one of [1] to [7],
in which the composition is a composition for forming an organic semiconductor layer.
[9] The composition according to any one of [1] to [8],
in which the composition is a composition for forming an organic semiconductor layer for an organic thin film transistor.

As shown above, according to the present invention, it is possible to provide a composition capable of manufacturing an organic thin film transistor having excellent carrier mobility even under low temperature conditions.

DESCRIPTION OF THE PREFERRED EMBODIMENTS

Figure 1:
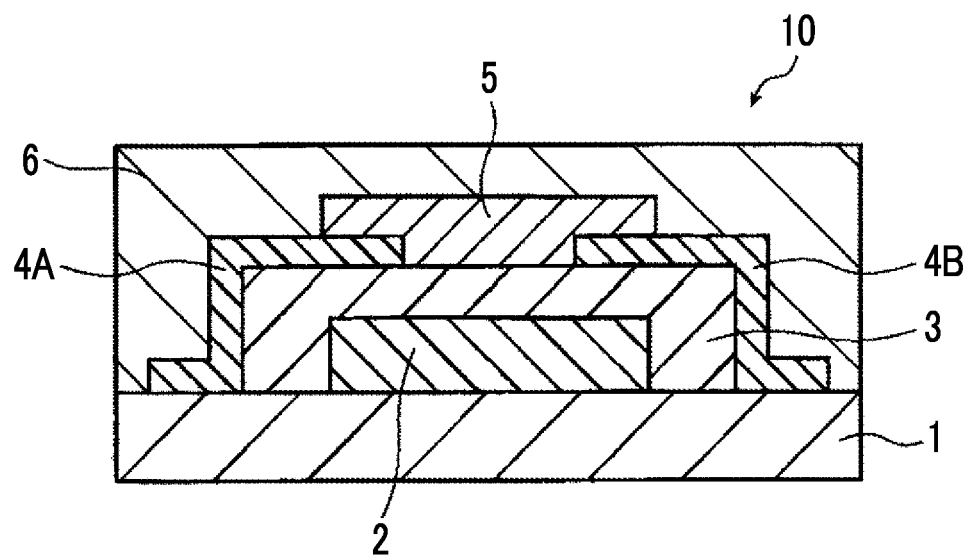
FIG. 1 is a schematic cross-sectional view showing a structure of a bottom gate-bottom contact type organic thin film transistor which is an example of an organic thin film transistor.

Hereinafter, the present invention will be described in detail.

In the present specification, the numerical range expressed by using "to" means a range including numerical values described before and after "to" as a lower limit value and an upper limit value.

In the present specification, unless otherwise specified, room temperature is intended to be 20° C.

In the present specification, unless otherwise specified, volume is a volume at room temperature.

In the present specification, the expression of a compound includes the compound itself, a salt thereof, and an ion thereof. A portion of the structure may be changed without deteriorating the desired effect.

In addition, a compound which is not specifically described as substituted or unsubstituted may have a substituent without deteriorating the desired effect. The same is also applied to a substituent, a linking group, and the like (hereinafter, referred to as a substituent and the like).

In the present specification, in a case of expressing "may", conditions expressed by "may" may or may not be satisfied. For example, "may have a substituent" also includes "may not have a substituent".

In the present specification, in a case where there are a plurality of substituents and the like represented by a specific symbol, or in a case where a plurality of substituents and the like are simultaneously defined, unless otherwise specified, respective substituents and the like may be identical to or different from each other. The same applies to the definition of the number of substituents and the like. In a case where a plurality of substituents and the like are near (particularly, adjacent to each other), unless otherwise specified, the substituents and the like may be linked to each other to form a ring.

In the present invention, in a case where the number of carbon atoms of a group is limited, the number of carbon atoms of the group means the total number of carbon atoms including a substituent, unless otherwise specified.

In the present specification, examples of a halogen atom include a fluorine atom, a chlorine atom, a bromine atom, and an iodine atom.

In the present invention, in a case where a group can form an acyclic skeleton and a cyclic skeleton, unless otherwise specified, the group includes an acyclic skeleton group and a cyclic skeleton group.

For example, an aliphatic hydrocarbon group, an alkyl group, and an alkenyl group include a group having any linear, branched, or cyclic structure, unless otherwise specified.

More specifically, the alkyl group includes a linear alkyl group, a branched alkyl group, and a cyclic (cyclo) alkyl group.

In a case where the group can form a cyclic skeleton, the lower limit of the number of atoms of the group forming the cyclic skeleton is 3 or more and preferably 5 or more, regardless of the lower limit of the number of atoms specifically described for this group. The above-described cycloalkyl group includes a bicycloalkyl group, a tricycloalkyl group, and the like.

A composition according to an embodiment of the present invention contains a compound represented by Formula (1) described later (hereinafter, also referred to as a specific compound) and an alcohol represented by Formula (S1) described later.

The mechanism by which the objects of the present invention are achieved by such a configuration is not entirely clear, but the present inventors consider as follows.

That is, the alcohol represented by Formula (S1) is a highly acidic fluorinated alcohol. A hydrogen atom in a hydroxyl group of the alcohol represented by Formula (S1) can form a hydrogen bond with a heteroatom (in particular, an oxygen atom which can be included as $X^{11}$ to $X^{14}$ and/or —N= which can be included as $B^{11}$ to $B^{18}$) in the specific compound, and the specific compound in the composition is solvated with the alcohol represented by Formula (S1). Therefore, solubility of the specific compound in the composition according to the embodiment of the present invention is good even at a low temperature (for example, room temperature). Due to such characteristics of the composition according to the embodiment of the present invention, even in a case where a temperature at which the composition is applied to produce an organic semiconductor film and the specific compound is precipitated is low, it is considered that crystallinity of the precipitated specific compound is good and carrier mobility of the obtained organic thin film transistor is improved.

In addition, in the composition according to the embodiment of the present invention, since the specific compound is well dissolved in the composition, it is easy to analysis the composition with liquid chromatography or the like, it is easy to confirm and/or adjust purity of the specific compound in the composition, and it is easy to improve performance and quality of the organic thin film transistor.

Compound Represented by Formula (1) (Specific Compound)

First, the compound represented by Formula (1) (specific compound) will be described.

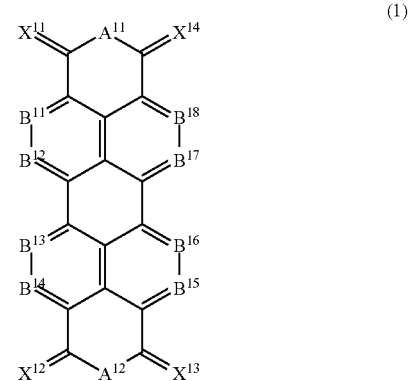

(1)

In Formula (1), $A^{11}$ and $A^{12}$ each represent —O—, —N($R^N$)—, or —P($R^N$)—. $A^{11}$ and $A^{12}$ are each preferably —N($R^N$)—. $A^{11}$ and $A^{12}$ may be the same or different from each other.

$R^N$ represents a hydrogen atom or a substituent.

The substituent which can be adopted as $R^N$ is not particularly limited. Examples thereof include a group selected from the following substituent group Z.

Substituent Group Z

Examples of the substituent group Z include a halogen atom, an alkyl group, an alkenyl group, an alkynyl group, an aryl group, a heterocyclic group, a silyl group, an alkoxy group, an amino group, an aryloxy group, an acyl group, an alkoxycarbonyl group, an aryloxycarbonyl group, an acyloxy group, an acylamino group, an aminocarbonylamino group, an alkoxycarbonylamino group, an aryloxycarbonylamino group, an alkylsulfonylamino group, an arylsulfonylamino group, an alkylthio group, an arylthio group, an alkylsulfinyl group, an arylsulfinyl group, an alkylsulfonyl group, an arylsulfonyl group, a silyloxy group, a heterocyclic oxy group, a carbamoyl group, a carbamoyloxy group, a heterocyclic thio group, a sulfamoyl group, an arylazo group, a heterocyclic azo group, an imide group, a phosphino group, a phosphinyl group, a phosphinyloxy group, a phosphinylamino group, a hydrazino group, an imino group, a cyano group, a hydroxy group, a nitro group, a mercapto group, a sulfo group, a carboxy group, a hydroxamic acid group, a sulfino group, a boronate group (—B(OH)$_2$), a phosphato group (—OPO(OH)$_2$), a phosphono group (—PO(OH)$_2$), and a sulfato group (—OSO$_3$H).

The group selected from the substituent group Z may further have a substituent.

Examples of the halogen atom included in the substituent group Z include a fluorine atom, a chlorine atom, a bromine atom, and an iodine atom, and a fluorine atom or a chlorine atom is preferable.

The alkyl group included in the substituent group Z is not particularly limited, but an alkyl group having 1 (3) to 30 carbon atoms is preferable, an alkyl group having 1 (3) to 20 carbon atoms is more preferable, and an alkyl group having 4 to 20 carbon atoms is still more preferable. The numbers in parentheses represent the number of carbon atoms in a case of a cycloalkyl group.

Examples of the alkyl group included in the substituent group Z, which may have a substituent, include a methyl group, an ethyl group, a propyl group, a 2-methylpropyl group, a butyl group, an amyl group, a pentyl group, a 1-methylpentyl group, a 2,2-dimethylpropyl group, a hexyl group, a heptyl group, an octyl group, a 2-ethylhexyl group, a nonyl group, a decyl group, a 3,7-dimethyloctyl group, an undecyl group, a dodecyl group, a tridecyl group, a tetradecyl group, a pentadecyl group, a 2,6-dimethyloctyl group, an icosyl group, a 2-decyltetradecyl group, a 2-hexyldodecyl group, a 2-ethyloctyl group, a 2-butyldecyl group, a 1-octylnonyl group, a 2-octyldecyl group, a 2-octyldodecyl group, a 7-hexylpentadecyl group, a 2-octyltetradecyl group, a cyclopropyl group, a cyclobutyl group, a cyclopentyl group, a cyclohexyl group, an adamantyl group, a benzyl group, a 2-cyclohexylethyl group, a p-chlorobenzyl group, a 2-phenylethyl group, a trifluoromethyl group, a perfluoroethyl group, 2,2,3,3,4,4,4,-heptafluorobutyl group, $C_5F_{11}C_2H_4$—, $C_6F_{13}C_2H_4$—, a 3-aminopropyl group, a 4-aminobutyl group, a 5-ethoxypentyl group, a (meth)acryloxypropyl group, a (meth)acryloxypentyl group, a 4-hydroxybutyl group, a 4-sulfobutyl group, a 10-phosphonodecyl group, a 2-hydroxyethoxymethyl group, a 2-imidazolylethoxymethyl group, a 4-(N,N-dimethylamino) butyl group, and a 5-norbornenemethyl group.

The alkenyl group included in the substituent group Z is not particularly limited, but an alkenyl group having 2 to 20 carbon atoms is preferable, an alkenyl group having 2 to 12 carbon atoms is more preferable, and an alkenyl group having 2 to 8 carbon atoms is still more preferable.

Examples of the alkenyl group included in the substituent group Z, which may have a substituent, include a vinyl group, an allyl group, a 2-butenyl group, a 1-pentenyl group, and a 4-pentenyl group.

The alkynyl group included in the substituent group Z is not particularly limited, but an alkynyl group having 2 to 20 carbon atoms is preferable, an alkynyl group having 2 to 12 carbon atoms is more preferable, and an alkynyl group having 2 to 8 carbon atoms is still more preferable.

Examples of the alkynyl group included in the substituent group Z, which may have a substituent, include an ethynyl group, a propargyl group, a 1-pentynyl group, a trimethylsilylethynyl group, a triethylsilylethynyl group, a tri-i-propylsilylethynyl group, and a 2-p-propylphenylethynyl group.

The aryl group included in the substituent group Z is not particularly limited, but an aryl group having 6 to 20 carbon atoms is preferable and an aryl group having 6 to 12 carbon atoms is more preferable.

Examples of the aryl group included in the substituent group Z, which may have a substituent, include a phenyl group, a naphthyl group, a 2,4,6-trimethylphenyl group, a p-(t-butyl)phenyl group, a 4-methyl-2,6-dipropylphenyl group, a 4-fluorophenyl group, a 4-trifluoromethylphenyl group, a p-pentylphenyl group, a 3,4-dipentylphenyl group, a p-heptoxyphenyl group, and a 3,4-diheptoxyphenyl group.

Examples of the heterocyclic group included in the substituent group Z include heterocyclic groups which have 3 or more atoms constituting the ring and include at least one or more heteroatoms and 1 to 30 carbon atoms as the atoms constituting the ring. In addition, the heterocyclic group includes an aromatic heterocyclic group (heteroaryl group) and an aliphatic heterocyclic group.

Examples of the hetero atom constituting the ring include a nitrogen atom, an oxygen atom, and a sulfur atom, and the number thereof is not particularly limited, but is, for example, 1 or 2. The number of carbon atoms constituting the ring is preferably 3 to 20 and more preferably 5 to 12.

As the heterocyclic group, a 5-membered ring, a 6-membered ring, or a group of a fused ring of these rings is preferable.

Examples of the heterocyclic group included in the substituent group Z include a thienyl group, a thiazolyl group, an imidazolyl group, a pyridyl group, a pyrimidinyl group, a quinolyl group, a furanyl group, a selenophenyl group, a piperidyl group, a morpholino group, a benzoxazolyl group, a benzimidazolyl group, a benzthiazolyl group, a 2-hexylfuranyl group, and a pyranyl group.

The silyl group included in the substituent group Z, which may have a substituent, is not particularly limited, but a silyl group which has a group selected from an alkyl group and an aryl group as a substituent and has 3 to 40 (more preferably 3 to 30 and still more preferably 3 to 24) carbon atoms is preferable.

Examples of the silyl group included in the substituent group Z, which may have a substituent, include a trimethylsilyl group, a triphenylsilyl group, and a dimethylphenylsilyl group.

The alkoxy group included in the substituent group Z is not particularly limited, but an alkoxy group having 1 to 20 carbon atoms is preferable, an alkoxy group having 1 to 12 carbon atoms is more preferable, and an alkoxy group having 1 to 8 carbon atoms is still more preferable.

Examples of the alkoxy group included in the substituent group Z include a methoxy group, an ethoxy group, and a butoxy group.

The amino group included in the substituent group Z, which may have a substituent, is not particularly limited, but an amino group or an amino group which have a group selected from an alkyl group and an aryl group as a substituent and has 1 to 20 (more preferably 1 to 10 and still more preferably 1 to 6) carbon atoms is preferable.

Examples of the amino group included in the substituent group Z, which may have a substituent, include an amino group, a methylamino group, a dimethylamino group, a diethylamino group, a dibenzylamino group, and an anilino group.

The aryloxy group included in the substituent group Z is not particularly limited, but an aryloxy group having 6 to 20 carbon atoms is preferable, an aryloxy group having 6 to 16 carbon atoms is more preferable, and an aryloxy group having 6 to 12 carbon atoms is still more preferable.

Examples of the aryloxy group included in the substituent group Z include a phenyloxy group and a 2-naphthyloxy group.

The acyl group included in the substituent group Z is not particularly limited, but an acyl group having 1 to 20 carbon atoms is preferable, an acyl group having 1 to 16 carbon atoms is more preferable, and an acyl group having 1 to 12 carbon atoms is still more preferable.

Examples of the acyl group included in the substituent group Z, which may have a substituent, include an acetyl group, a hexanoyl group, a benzoyl group, a formyl group, and a pivaloyl group.

The alkoxycarbonyl group included in the substituent group Z is not particularly limited, but an alkoxycarbonyl group having 2 to 20 carbon atoms is preferable, an alkoxycarbonyl group having 2 to 16 carbon atoms is more preferable, an alkoxycarbonyl group having 2 to 12 carbon atoms is still more preferable, and a methoxycarbonyl group or an ethoxycarbonyl group is particularly preferable.

The aryloxycarbonyl group included in the substituent group Z is not particularly limited, but an aryloxycarbonyl group having 7 to 20 carbon atoms is preferable, an aryloxycarbonyl group having 7 to 16 carbon atoms is more preferable, an aryloxycarbonyl group having 7 to 10 carbon atoms is still more preferable, and a phenyloxycarbonyl group is particularly preferable.

The acyloxy group included in the substituent group Z is not particularly limited, but an acyloxy group having 2 to 20 carbon atoms is preferable, an acyloxy group having 2 to 16 carbon atoms is more preferable, and an acyloxy group having 2 to 10 carbon atoms is still more preferable.

Examples of the acyloxy group included in the substituent group Z, which may have a substituent, include an acetoxy group, a benzoyloxy group, and a (meth)acryloyloxy group.

The acylamino group included in the substituent group Z is not particularly limited, but an acylamino group having 2 to 20 carbon atoms is preferable, an acylamino group having 2 to 16 carbon atoms is more preferable, and an acylamino group having 2 to 10 carbon atoms is still more preferable.

Examples of the acylamino group included in the substituent group Z include an acetylamino group and a benzoylamino group.

The aminocarbonylamino group included in the substituent group Z is not particularly limited, but an aminocarbonylamino group having 2 to 20 carbon atoms is preferable, an aminocarbonylamino group having 2 to 16 carbon atoms is more preferable, an aminocarbonylamino group having 2 to 12 carbon atoms is still more preferable, and a ureido group is particularly preferable.

The alkoxycarbonylamino group included in the substituent group Z is not particularly limited, but an alkoxycarbonylamino group having 2 to 20 carbon atoms is preferable, an alkoxycarbonylamino group having 2 to 16 carbon atoms is more preferable, an alkoxycarbonylamino group having 2 to 12 carbon atoms is still more preferable, and a methoxycarbonylamino group is particularly preferable.

The aryloxycarbonylamino group included in the substituent group Z is not particularly limited, but an aryloxycarbonylamino group having 7 to 20 carbon atoms is preferable, an aryloxycarbonylamino group having 7 to 16 carbon atoms is more preferable, an aryloxycarbonylamino group having 7 to 12 carbon atoms is still more preferable, and a phenyloxycarbonylamino group is particularly preferable.

The alkylthio group included in the substituent group Z is not particularly limited, but an alkylthio group having 1 to 20 carbon atoms is preferable, an alkylthio group having 1 to 16 carbon atoms is more preferable, and an alkylthio group having 1 to 12 carbon atoms is still more preferable. Examples of the alkylthio group included in the substituent group Z include a methylthio group, an ethylthio group, and an octylthio group.

The arylthio group included in the substituent group Z is not particularly limited, but an arylthio group having 6 to 20 carbon atoms is preferable, an arylthio group having 6 to 16 carbon atoms is more preferable, an arylthio group having 6 to 12 carbon atoms is still more preferable, and a phenylthio group is particularly preferable.

The above-described group selected from the substituent group Z may further have a substituent. Examples of such a substituent include a group selected from the substituent group Z.

In the group which further has a substituent (also referred to as a group obtained by combining these substituents), the number of substituents which may be further included is not particularly limited, but for example, preferably 1 to 6 and more preferably 1 to 3.

The group obtained by combining these substituents is not particularly limited, and examples thereof include a group obtained by substituting each of the preferred groups selected from the substituent group Z with another group selected from the substituent group Z. Specific examples thereof include an alkyl group having, as a substituent, a group selected from the group consisting of a halogen atom, an alkyl group, an aryl group, a heterocyclic group (heteroaryl group), an alkoxy group (including a hydroxyalkoxy group, a halogenated alkoxy group, and a heteroarylalkoxy group), an amino group, an acyloxy group, a hydroxy group, a sulfate group, a silyl group, a (meth)acryloyloxy group, and a phosphono group; and an alkynyl group having, as a substituent, a halogenated aryl group, a (fluorinated) alkyl aryl group, or a silyl group. Further, examples thereof also include a group obtained by removing one hydrogen atom from the compound represented by Formula (1).

More specifically, examples thereof include the group described as the examples of the above-described substituent group Z, an exemplary compound described below, or a group in a compound used in Examples.

Among these, as the group obtained by combining these substituents, an alkyl group having a halogen atom as a substituent (alkyl halide group), an alkyl group having a heterocyclic group as a substituent, or an alkyl group having an aryl group as a substituent is preferable, an alkyl group having a fluorine atom as a substituent (alkyl fluoride group), an alkyl group having a heterocyclic group as a substituent, or an alkyl group having an aryl group as a substituent is more preferable, and an alkyl group having an aryl group as a substituent is still more preferable.

As the group selected from the above-described substituent group Z, which can be adopted as $R^N$, an alkyl group, an aryl group, an alkenyl group, an alkynyl group, a heterocyclic group, or a silyl group is preferable, an alkyl group (preferably having 1 to 20 carbon atoms), an aryl group (preferably having 6 to 20 carbon atoms), or a heteroaryl group (including at least one or more heteroatom as a ring-constituting atom; preferably a group of a 5-membered ring, a 6-membered ring, or a fused ring thereof; the number of ring-constituting carbon atoms is preferably 3 to 20) is more preferable, and an alkyl group (preferably having 4 to 20 carbon atoms) is still more preferable.

Among these, as the substituent which can be adopted as $R^N$, an unsubstituted alkyl group, an alkyl halide group, an alkyl group having an aryl group as a substituent, or an alkyl group having a hetero ring as a substituent is more preferable.

In a case where $A^{11}$ and $A^{12}$ each have $R^N$, two $R^N$'s may be identical to or different from each other.

In Formula (1), $B^{11}$ to $B^{18}$ each represent —N═ or —C($R^M$)═. Here, $R^M$ represents a hydrogen atom or a substituent.

The substituent which can be adopted as $R^M$ is not particularly limited, and examples thereof include a group selected from the above-described substituent group Z. The group selected from the substituent group Z may further have a substituent. Examples of such a substituent include a group selected from the substituent group Z. Examples of the group which further has a substituent include the above-described group obtained by combining the substituents, which can be adopted as $R^N$. Specific examples thereof include the above-described group and a group having a methine group bonded to a carbon atom of the compound represented by Formula (1).

Among these, as the substituent which can be adopted as $R^M$, an alkyl group, an alkenyl group, an alkynyl group, an alkoxycarbonyl group, an aryl group, an alkoxy group, a heterocyclic group (particularly, a heteroaryl group), an amino group, a halogen atom, a cyano group, a carboxy group, a nitro group, or a mercapto group is preferable; an alkyl group (unsubstituted alkyl group, alkyl group having an aryl group as a substituent, alkyl group having a hetero ring as a substituent, or the like), an alkenyl group (unsubstituted alkenyl group, alkenyl group having a silyl group as a substituent, alkenyl group having an aryl group as a substituent, alkenyl group having a hetero ring as a substituent, or the like), an alkynyl group (unsubstituted alkynyl group, alkynyl group having a silyl group as a substituent, alkynyl group having an aryl group as a substituent, alkynyl group having a hetero ring as a substituent, or the like), an aryl group, an alkoxy group, a heterocyclic group (particularly, a heteroaryl group), a halogen atom, or a cyano group is more preferable; an unsubstituted alkyl group, an alkenyl group (unsubstituted alkenyl group, alkenyl group having a silyl group as a substituent, alkenyl group having an aryl group as a substituent, alkenyl group having a hetero ring as a substituent, or the like), an alkynyl group (unsubstituted alkynyl group, alkynyl group having a silyl group as a substituent, alkynyl group having an aryl group as a substituent, alkynyl group having a hetero ring as a substituent, or the like), an aryl group, a heterocyclic group (particularly, a heteroaryl group), a halogen atom, or a cyano group is still more preferable.

The substituent which can be adopted as $R^M$ may form a ring. Examples of an aspect in which the substituent forms a ring include an aspect in which substituents are bonded to each other to form a ring and an aspect in which one atom is shared by a plurality of substituents to form a ring.

Examples of the aspect in which substituents are bonded to each other to form a ring include an aspect in which two vinyl groups are bonded to each other to form a benzene ring together with a carbon atom to which $R^M$ is bonded. In addition, examples of the aspect in which one atom is shared by a plurality of substituents to form a ring include an aspect in which two substituents are combined to form a sulfur atom (—S— group).

It is preferable that at least one of $B^{11}$, $B^{12}$, $B^{13}$, $B^{14}$, $B^{15}$, $B^{16}$, $B^{17}$, or $B^{18}$ is —N═, it is more preferable that one to six of $B^{11}$ to $B^{18}$ are —N═, it is still more preferable that one or two of $B^{11}$ to $B^{18}$ are —N═, and it is particularly preferable that two of $B^{11}$ to $B^{18}$ are —N═.

B which can adopt —N═ is not particularly limited, and any of $B^{11}$ to $B^{18}$ may be —N═. For example, it is preferable that at least one of $B^{12}$, $B^{13}$, $B^{16}$, or $B^{17}$ is —N═, and it is more preferable that any one or both of $B^{12}$ and $B^{16}$ is —N═.

In —N═ which can be adopted as $B^{11}$ to $B^{18}$, the nitrogen atom may have a substituent. Examples thereof include an N-oxide group (N→O group) and a salt having a counter anion.

In Formula (1), $X^{11}$ to $X^{14}$ each represent an oxygen atom or a sulfur atom, and an oxygen atom is preferable. It is more preferable that all of $X^{11}$ to $X^{14}$ is an oxygen atom.

Here, a combination of $A^{11}$ and $A^{12}$, and $X^{11}$ to $X^{14}$ is not particularly limited, but is preferably a combination in which $A^{11}$ and $A^{12}$ are —N($R^N$)— and $X^{11}$ to $X^{14}$ are oxygen atoms.

The specific compound is preferably a compound represented by Formula (2).

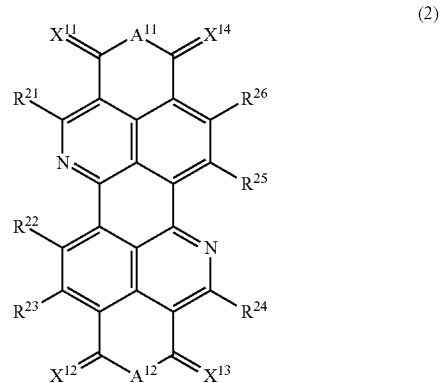

(2)

In Formula (2), $A^{11}$, $A^{12}$, and $X^{11}$ to $X^{14}$ each have the same meaning as $A^{11}$, $A^{12}$, and $X^{11}$ to $X^{14}$ in Formula (1), and preferred aspects thereof are also the same. In addition, preferred combinations of $A^{11}$, $A^{12}$, and $X^{11}$ to $X^{14}$ are also as described above.

$R^{21}$ to $R^{26}$ each represent a hydrogen atom or a substituent. The substituent which can be adopted as $R^{21}$ to $R^{26}$ is the same meaning as the substituent which can be adopted as $R^M$, and preferred aspects thereof are also the same. In order to form a ring, $R^{21}$ to $R^{26}$ may be bonded to each other, or may be bonded to a carbon atom forming an isoquinolino quinoline skeleton.

Specific examples of the specific compound are shown below and Examples, but the present invention is not limited thereto.

In the specific examples below, compounds in which $A^{11}$ and $A^{12}$ are both —N($R^N$)— are shown, but the specific examples below also include compounds in which one or both of $A^{11}$ and $A^{12}$ (N—$R^{N1}$ and N—$R^{N2}$ in the specific examples below) are replaced with —O— or —P($R^N$)—. Here, examples of $R^N$ in —P($R^N$)— include the same group as $R^{N1}$ or $R^{N2}$ in the specific examples below.

In the specific examples below, TIPS represents a triisopropylsilyl group, and * represents a bonding site. $R^{N1}$ of the compound Nos. 18, 53, 78 is —$C_7H_{13}(C_6H_{13})C_8H_{17}$. $R^{N1}$ and $R^{N2}$ of the compound No. 3, $R^{27}$ of the compound No. 20, $R^{N2}$ of the compound No. 28, $R^{N1}$ and $R^{N2}$ of the compound No. 38, $R^{22}$ of the compound No. 55, $R^{N1}$ and $R^{N2}$ of the compound No. 63, $R^{22}$ of the compound No. 80, $R^{N2}$ of the compound No. 88, $R^{N2}$ of the compound No. 98, $R^{N1}$ and $R^{N2}$ of the compound No. 108, and $R^{N1}$ and $R^{N2}$ of the compound No. 133 are -$nC_6H_{13}$.

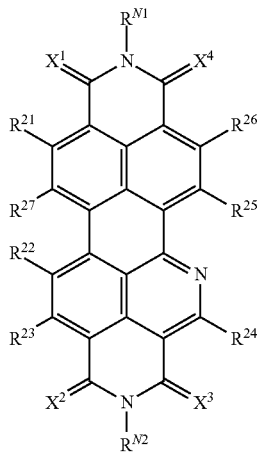

| No. | $X^1$ | $X^2$ | $X^2$ | $X^4$ | $R^{21}$ | $R^{27}$ | $R^{22}$ | $R^{23}$ | $R^{24}$ | $R^{25}$ | $R^{26}$ | $R^{N1}$ | $R^{N2}$ |
|---|---|---|---|---|---|---|---|---|---|---|---|---|---|
| 1 | O | O | O | O | H | H | H | H | H | H | H | H | H |
| 2 | O | O | O | O | H | H | H | H | H | H | H | $CH_3$ | $CH_3$ |
| 3 | O | O | O | O | H | H | H | H | H | H | H | $nC_6H_{13}$ | $nC_6H_{13}$ |
| 4 | O | O | O | O | H | H | H | H | H | H | H | *-cyclohexyl | *-cyclohexyl |
| 5 | S | S | O | O | H | H | H | H | H | H | H | *-cyclohexyl | *-cyclohexyl |
| 6 | O | O | S | S | H | H | H | H | H | H | H | *-cyclohexyl | *-cyclohexyl |
| 7 | O | S | S | O | H | H | H | H | H | H | H | *-cyclohexyl | *-cyclohexyl |
| 8 | O | O | O | O | H | H | H | H | H | H | H | $CH_2C_3F_7$ | $CH_2C_3F_7$ |
| 9 | O | O | O | O | H | H | H | H | H | H | H | -isoPropyl | -isoPropyl |
| 10 | O | O | O | O | H | H | H | H | H | H | H | -tert-Butyl | -tert-Butyl |
| 11 | S | S | O | O | H | H | H | H | H | H | H | *-CH($C_8H_{17}$)($C_8H_{17}$) | *-CH($C_8H_{17}$)($C_8H_{17}$) |
| 12 | O | O | O | O | H | H | H | H | H | H | H | *-CH($C_8H_{17}$)($C_8H_{17}$) | *-CH($C_8H_{17}$)($C_{10}H_{21}$) |
| 13 | O | O | O | O | H | H | H | H | H | H | H | $C_2H_4C_5F_{11}$ | $C_2H_4C_5F_{11}$ |
| 14 | O | O | O | O | Cl | Cl | Cl | Cl | Cl | Cl | Cl | *-cyclohexyl | *-cyclohexyl |
| 15 | O | O | O | O | F | H | H | H | F | H | H | *-phenyl | *-phenyl |

-continued
| # | | | | | | | | | | | | |
|---|---|---|---|---|---|---|---|---|---|---|---|---|
| 16 | O | O | O | O | F | F | F | F | F | F | F | 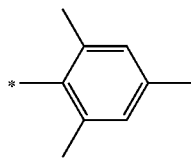 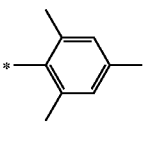 |
| 17 | O | O | O | O | CN | H | H | H | H | H | CN | 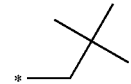 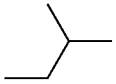 |
| 18 | O | O | O | O | Br | H | H | H | H | H | H | 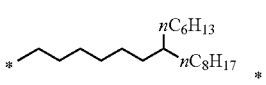 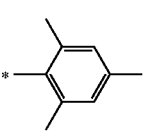 |
| 19 | O | O | O | O | $NO_2$ | H | H | H | H | H | H | 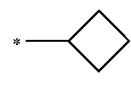 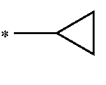 |
| 20 | O | O | O | O | $CH_3$ | $nC_6H_{13}$ | H | H | H | H | H | 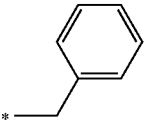 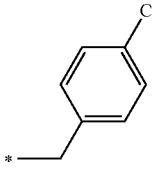 |
| 21 | O | O | O | O | $CO_2CH_3$ | H | H | H | H | H | H | 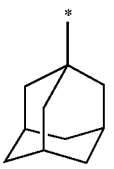 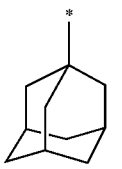 |
| 22 | O | O | O | O | H | -Ph | H | H | H | -Ph | H | 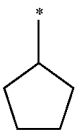 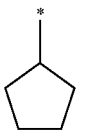 |
| 23 | O | O | O | O | —COOH | H | H | H | H | H | H | $CF_3$ / $C_2F_5$ |
| 24 | O | O | O | O | H | $CF_3$ | H | H | H | H | H | 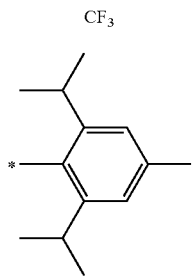  |
| 25 | O | O | O | O | $OCH_3$ | H | H | H | H | H | H | 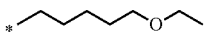 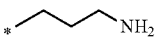 |
| 26 | O | O | O | O | H | H | H | H | H | H | H | H / H |
| 27 | O | O | O | O | H | H | H | H | H | H | H | $CH_3$ / $CH_3$ |
| 28 | O | O | O | O | H | H | H | H | H | H | H |  $nC_6H_{13}$ |
| 29 | O | O | O | O | H | H | H | H | H | H | H | 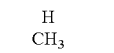  |
| 30 | S | S | O | O | H | H | H | H | H | H | H | $nC_{10}H_{21}$ / $nC_{10}H_{21}$ |

-continued

| No. | X¹ | X² | X³ | X⁴ | R²¹ | R²² | R²³ | R²⁴ | R²⁵ | R²⁶ | R$^{N1}$ | R$^{N2}$ |
|---|---|---|---|---|---|---|---|---|---|---|---|---|
| 31 | O | O | S | S | H | H | H | H | H | H |  |  |
| 32 | O | S | S | O | H | H | H | H | H | H | 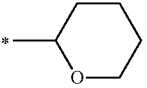 | 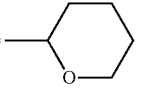 |
| 33 | O | O | O | O |  | H | H | H |  | H | 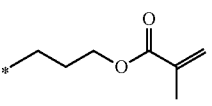 | CH₂C₃F₇ |
| 34 | O | O | O | O | H |  | H |  | H | H | -isoPropyl | -isoPropyl |
| 35 | O | O | O | O | H | H | H | H | H | H | 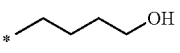 | 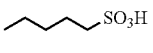 |

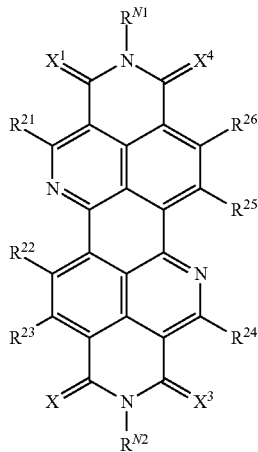

| No. | X¹ | X² | X³ | X⁴ | R²¹ | R²² | R²³ | R²⁴ | R²⁵ | R²⁶ | R$^{N1}$ | R$^{N2}$ |
|---|---|---|---|---|---|---|---|---|---|---|---|---|
| 36 | O | O | O | O | H | H | H | H | H | H | H | H |
| 37 | O | O | O | O | H | H | H | H | H | H | CH₃ | CH₃ |
| 38 | O | O | O | O | H | H | H | H | H | H | nC₆H₁₃ | nC₆H₁₃ |
| 39 | O | O | O | O | H | H | H | H | H | H | 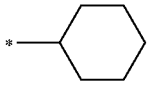 | 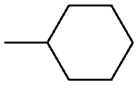 |
| 40 | S | S | O | O | H | H | H | H | H | H | 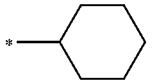 | 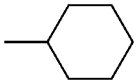 |
| 41 | O | O | S | S | H | H | H | H | H | H | 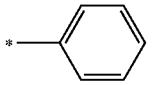 | 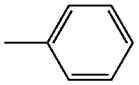 |
| 42 | O | S | S | O | H | H | H | H | H | H | 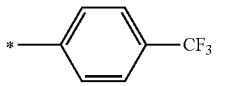 | 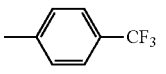 |
| 43 | O | O | O | O | H | H | H | H | H | H | CH₂C₃F₇ | CH₂C₃F₇ |
| 44 | O | O | O | O | H | H | H | H | H | H | -isoPropyl | -isoPropyl |
| 45 | O | O | O | O | H | H | H | H | H | H | -tert-Butyl | -tert-Butyl |

-continued
| | | | | | | | | | | | |
|---|---|---|---|---|---|---|---|---|---|---|---|
| 46 | S | S | O | O | H | H | H | H | H | H | 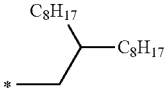 | 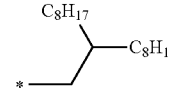 |
| 47 | O | O | O | O | H | H | H | H | H | H | 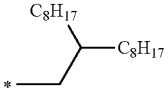 | 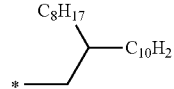 |
| 48 | O | O | O | O | H | H | H | H | H | H | $C_2H_4C_5F_{11}$ | $C_2H_4C_5F_{11}$ |
| 49 | O | O | O | O | Cl | Cl | Cl | Cl | Cl | Cl | 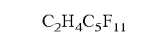 | 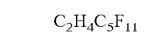 |
| 50 | O | O | O | O | H | F | H | H | F | H | 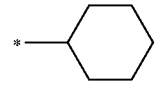 | 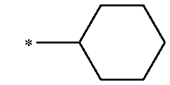 |
| 51 | O | O | O | O | F | F | F | F | F | F | 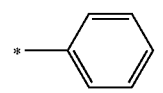 | 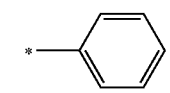 |
| 52 | O | O | O | O | H | CN | H | H | CN | H | 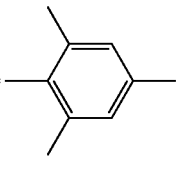 | 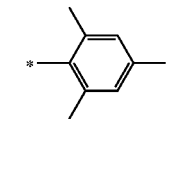 |
| 53 | O | O | O | O | Br | H | H | H | H | H | 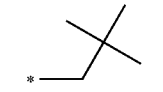 | 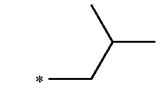 |
| 54 | O | O | O | O | $NO_2$ | H | H | H | H | H | 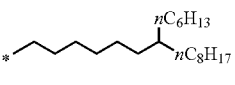 | 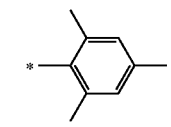 |
| 55 | O | O | O | O | $CH_3$ | $nC_6H_{13}$ | H | H | H | H | 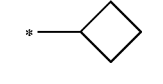 | 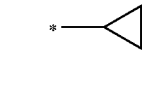 |
| 56 | O | O | O | O | $CO_2CH_3$ | H | H | H | H | H | 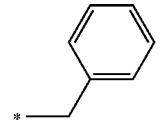 | 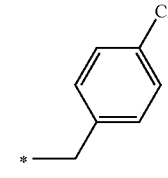 |
| 57 | O | O | O | O | H | -Ph | H | H | H | -Ph | 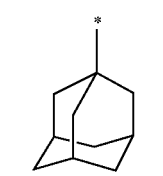 | 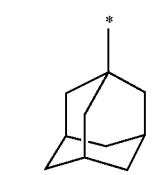 |
| 58 | O | O | O | O | —COOH | H | H | H | H | H | $CF_3$ | $C_2F_5$ |

| # | | | | | | | | | | | | |
|---|---|---|---|---|---|---|---|---|---|---|---|---|
| 59 | O | O | O | O | H | CF₃ | H | H | H | H | 2,6-diisopropyl-4-methylphenyl (*) | 4-tert-butylphenyl (*) |
| 60 | O | O | O | O | OCH₃ | H | H | H | H | H | *-(CH₂)₄-O-C₂H₅ | *-(CH₂)₃-NH₂ |
| 61 | O | O | O | O | H | H | H | H | H | H | H | H |
| 62 | O | O | O | O | H | H | H | H | H | H | CH₃ | CH₃ |
| 63 | O | O | O | O | H | H | H | H | H | H | nC₆H₁₃ | nC₆H₁₃ |
| 64 | O | O | O | O | H | H | H | H | H | H | cyclohexyl (*) | cyclohexyl (*) |
| 65 | S | S | O | O | H | H | H | H | H | H | cyclohexyl (*) | cyclohexyl (*) |
| 66 | O | O | S | S | H | H | H | H | H | H | cyclohexyl (*) | cyclohexyl (*) |
| 67 | O | S | S | O | H | H | H | H | H | H | cyclohexyl (*) | cyclohexyl (*) |
| 68 | O | O | O | O | H | H | H | H | H | H | CH₂C₃F₇ | CH₂C₃F₇ |
| 69 | O | O | O | O | H | H | H | H | H | H | -isoPropyl | -isoPropyl |
| 70 | O | O | O | O | H | H | H | H | H | H | -tert-Butyl | -tert-Butyl |
| 71 | S | S | O | O | H | H | H | H | H | H | *-CH₂-CH(C₈H₁₇)(C₈H₁₇) | *-CH₂-CH(C₈H₁₇)(C₈H₁₇) |
| 72 | O | O | O | O | H | H | H | H | H | H | *-CH₂-CH(C₈H₁₇)(C₈H₁₇) | *-CH₂-CH(C₈H₁₇)(C₁₀H₂₁) |
| 73 | O | O | O | O | H | CF₃ | H | H | H | H | C₂H₄C₅F₁₁ | C₂H₄C₅F₁₁ |
| 74 | O | O | O | O | Cl | Cl | Cl | Cl | Cl | Cl | cyclohexyl (*) | cyclohexyl (*) |
| 75 | O | O | O | O | F | H | H | H | F | H | phenyl (*) | phenyl (*) |
| 76 | O | O | O | O | F | F | F | F | F | F | 2,4,6-trimethylphenyl (*) | 2,4,6-trimethylphenyl (*) |
| 77 | O | O | O | O | CN | H | H | H | CN | H | *-CH₂-C(CH₃)₃ | *-CH₂-CH(CH₃)₂ |

-continued

| # | | | | | | | | | | | | |
|---|---|---|---|---|---|---|---|---|---|---|---|---|
| 78 | O | O | O | O | Br | H | H | H | H | H | *—(CH₂)₆—CH(nC₆H₁₃)(nC₈H₁₇) | 2,4,6-trimethylphenyl |
| 79 | O | O | O | O | NO₂ | H | H | H | H | H | *-cyclobutyl | *-cyclopropyl |
| 80 | O | O | O | O | CH₃ | nC₆H₁₃ | H | H | H | H | *-CH₂-phenyl | *-CH₂-(4-Cl-phenyl) |
| 81 | O | O | O | O | CO₂CH₃ | H | H | H | H | H | 1-adamantyl | 1-adamantyl |
| 82 | O | O | O | O | H | Ph | H | H | H | Ph | *-cyclopentyl | *-cyclopentyl |
| 83 | O | O | O | O | —COOH | H | H | H | H | H | CF₃ | C₂F₅ |
| 84 | O | O | O | O | H | CF₃ | H | H | H | H | 2,6-diisopropyl-4-methylphenyl | *-(4-tBu-phenyl) |
| 85 | O | O | O | O | OCH₃ | H | H | H | H | H | *—(CH₂)₅—O—C₂H₅ | *—(CH₂)₃—NH₂ |
| 86 | O | O | O | O | H | H | H | H | H | H | H | H |
| 87 | O | O | O | O | H | H | H | H | H | H | CH₃ | CH₃ |
| 88 | O | O | O | O | H | H | H | H | H | H | *—(CH₂)₃—CH=CH₂ | nC₆H₁₃ |
| 89 | O | O | O | O | H | H | H | H | H | H | *-cyclohexyl | *-cyclohexyl |
| 90 | S | S | O | O | H | H | H | H | H | H | nC₁₀H₂₁ | nC₁₀H₂₁ |
| 91 | O | O | S | S | H | H | H | H | H | H | *-cyclohexyl | *-cyclohexyl |
| 92 | O | S | S | O | H | H | H | H | H | H | *-tetrahydropyran-2-yl | *-tetrahydropyran-2-yl |

-continued

| # | | | | | | | | | | | | |
|---|---|---|---|---|---|---|---|---|---|---|---|---|
| 93 | O | O | O | O | *-thiophen-2-yl | H | H | H | H | *-thiophen-2-yl | *-(CH₂)₃-O-C(=O)-C(CH₃)=CH₂ | CH₂C₃F₇ |
| 94 | O | O | O | O | H | *-isothiazol-3-yl | H | H | *-furan-3-yl | H | -isoPropyl | -isoPropyl |
| 95 | O | O | O | O | H | H | H | H | H | H | *-(CH₂)₄-OH | *-(CH₂)₄-SO₃H |
| 96 | O | O | O | O | H | H | H | H | H | H | H | H |
| 97 | O | O | O | O | H | H | H | H | H | H | CH₃ | CH₃ |
| 98 | O | O | O | O | H | H | H | H | H | H | *-(CH₂)₃-CH=CH₂ | nC₆H₁₃ |
| 99 | O | O | O | O | H | H | H | H | H | H | *-cyclohexyl | *-cyclohexyl |
| 100 | S | S | O | O | H | H | H | H | H | H | nC₁₀H₂₁ | nC₁₀H₂₁ |
| 101 | O | O | S | S | H | H | H | H | H | H | *-cyclohexyl | *-cyclohexyl |
| 102 | O | S | S | O | H | H | H | H | H | H | *-tetrahydropyran-2-yl | *-tetrahydropyran-2-yl |
| 103 | O | O | O | O | *-thiophen-2-yl | H | H | H | H | *-thiophen-2-yl | *-(CH₂)₃-O-C(=O)-C(CH₃)=CH₂ | CH₂C₃F₇ |
| 104 | O | O | O | O | H | *-isothiazol-3-yl | H | H | *-furan-3-yl | H | -isoPropyl | -isoPropyl |
| 105 | O | O | O | O | H | H | H | H | H | H | *-(CH₂)₄-OH | *-(CH₂)₄-SO₃H |
| 106 | O | O | O | O | H | H | H | H | H | H | H | H |
| 107 | O | O | O | O | H | H | H | H | H | H | CH₃ | CH₃ |
| 108 | O | O | O | O | Cl | H | H | H | H | H | nC₆H₁₃ | nC₆H₁₃ |
| 109 | O | O | O | O | F | H | H | H | H | H | *-cyclohexyl | *-cyclohexyl |
| 110 | S | S | O | O | CN | H | H | H | H | H | *-cyclohexyl | *-cyclohexyl |

-continued
| | | | | | | | | | | | | |
|---|---|---|---|---|---|---|---|---|---|---|---|---|
| 111 | O | O | S | S | —N(CH$_3$)$_2$ | H | H | H | H | H | 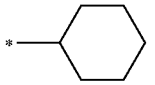 | 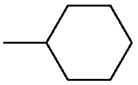 |
| 112 | O | S | S | O | H | H | H | H | H | H | 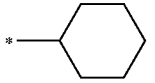 | 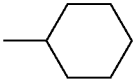 |
| 113 | O | O | O | O | H | H | H | H | H | 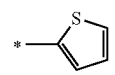 | CH$_2$C$_3$F$_7$ | CH$_2$C$_3$F$_7$ |
| 114 | O | O | O | O | H |  | H | H |  | H | -isoPropyl | -isoPropyl |
| 115 | O | O | O | O | H | H | H | H | H | H | -tert-Butyl | -tert-Butyl |
| 116 | S | S | O | O | H | H | H | H | H | H | 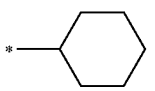 | 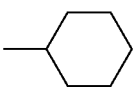 |
| 117 | O | O | O | O | H | H | H | H | H | H | 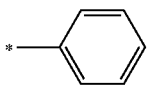 | 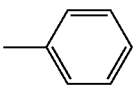 |
| 118 | O | O | O | O | H | H | H | H | H | H | C$_2$H$_4$C$_5$F$_{11}$ | C$_2$H$_4$C$_5$F$_{11}$ |
| 119 | O | O | O | O | Cl | H | Cl | H | H | H | 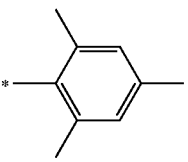 | 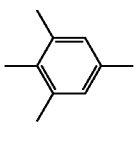 |
| 120 | O | O | O | O | F | H | F | H | H | H |  | 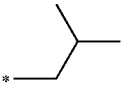 |
| 121 | O | O | O | O | F | F | F | F | F | F | 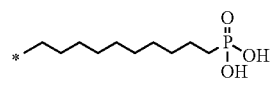 | 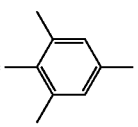 |
| 122 | O | O | O | O | CN | H | H | H | H | H |  |  |
| 123 | O | O | O | O | Br | H | H | H | H | Br |  |  |

-continued
| | | | | | | | | | | | | |
|---|---|---|---|---|---|---|---|---|---|---|---|---|
| 124 | O | O | O | O | NO₂ | H | H | H | H | H | 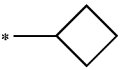 | 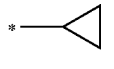 |
| 125 | O | O | O | O | CH₃ | H | H | H | H | H | 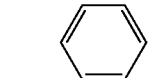 | 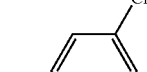 |
| 126 | O | O | O | O | CO₂CH₃ | H | H | H | H | H |  |  |
| 127 | O | O | O | O | H | H | H | H | H | H | 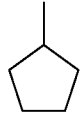 | 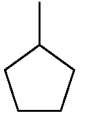 |
| 128 | O | O | O | O | —COOH | H | H | H | H | H | CF₃ | C₂F₅ |
| 129 | O | O | O | O | H | H | H | H | H | H | 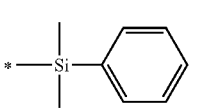 |  |
| 130 | O | O | O | O | OCH₃ | H | H | H | H | H | 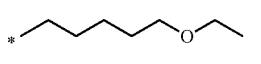 | 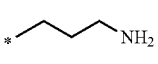 |
| 131 | O | O | O | O | H | H | H | H | H | H | H | H |
| 132 | O | O | O | O | CN | H | H | H | H | H | CH₂ | CH₃ |
| 133 | O | O | O | O | Br | H | H | H | H | Br | nC₆H₁₃ | nC₆H₁₃ |
| 134 | O | O | O | O | NO₂ | H | H | H | H | H | 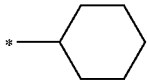 | 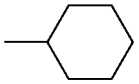 |
| 135 | S | S | O | O | CH₃ | H | H | H | H | H | nC₁₃H₂₇ | nC₂₀H₄₁ |
| 136 | O | O | S | S | CO₂CH₂ | H | H | H | H | H | 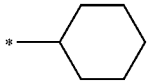 | 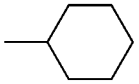 |
| 137 | O | S | S | O | H | H | H | H | H | H | 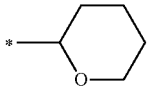 | 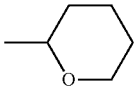 |
| 138 | O | O | O | O | —COOH | H | H | H | H | H | 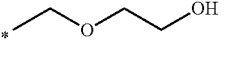 | 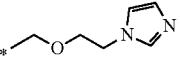 |
| 139 | O | O | O | O | H | H | H | H | H | H | 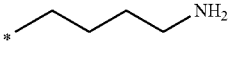 | 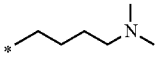 |
| 140 | O | O | O | O | OCH₃ | H | H | H | H | H | 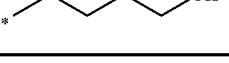 | 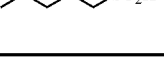 |

In addition, examples thereof also include compounds in which, in the compound Nos. 131 to 140, $R^{N1}$ and/or $R^{N2}$ is a 2-phenylethyl group (—CH$_2$—CH$_2$-Ph).
The compounds shown in Nos. 141 to 232 are compounds having the following central structure.
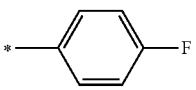
| No. | $R^{22}$ | $R^{25}$ | $R^{N1}$ | $R^{N2}$ |
|---|---|---|---|---|
| 141 | H | H | 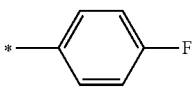 | 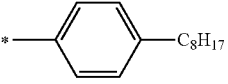 |
| 142 | H | H | CF$_3$ | CF$_3$ |
| 143 | H | H | nC$_8$H$_{17}$ | nC$_8$H$_{17}$ |
| 144 | H | H | nC$_{10}$H$_{21}$ | nC$_{10}$H$_{21}$ |
| 145 | H | H | 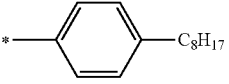 | 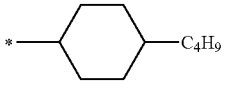 |
| 146 | H | H | 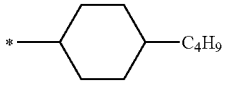 |  |
| 147 | H | H |  | 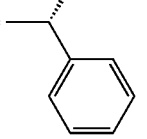 |
| 148 | H | H | 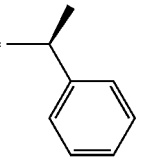 | 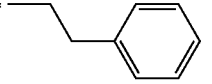 |
| 149 | H | H | 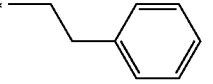 | 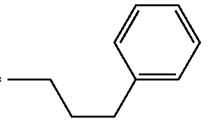 |
| 150 | H | H | 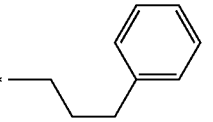 | 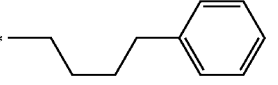 |
| 151 | H | H | 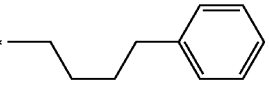 | |

-continued

[Core structure: a fused polycyclic aromatic diimide with substituents $R^{N1}$, $R^{N2}$ on the imide nitrogens, and $R^{22}$, $R^{25}$ on the aromatic core]

| No. | $R^{22}$ | $R^{25}$ | $R^{N1}$ | $R^{N2}$ |
|---|---|---|---|---|
| 152 | H | H | *-CH(CH₃)-CH₂-phenyl (isobutylbenzyl) | *-CH(CH₃)-CH₂-phenyl |
| 153 | H | H | *-(S)-CH(CH₃)-CH₂-phenyl | *-(R)-CH(CH₃)-CH₂-phenyl |
| 154 | H | H | *-CH₂CH₂-(pentafluorophenyl) | *-CH₂CH₂-(pentafluorophenyl) |
| 155 | H | H | *-CH₂CH₂-(tetrafluoro-4-C₈H₁₇-phenyl) | *-CH₂CH₂-(tetrafluoro-4-C₈H₁₇-phenyl) |
| 156 | H | H | *-CH₂CH₂-(4-pyridyl) | *-CH₂CH₂-(4-pyridyl) |
| 157 | H | H | *-CH₂CH₂-(3-pyridyl) | *-CH₂CH₂-(3-pyridyl) |
| 158 | H | H | *-CH₂CH₂-(2-pyrimidinyl) | *-CH₂CH₂-(2-pyrimidinyl) |
| 159 | H | H | *-CH₂CH₂-(4-(N-C₁₀H₂₁)pyridinium) I⁻ | *-CH₂CH₂-(4-(N-C₁₀H₂₁)pyridinium) I⁻ |

-continued

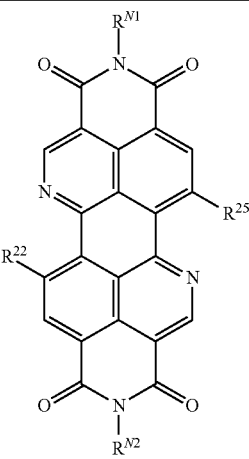

| No. | R²² | R²⁵ | RN¹ | RN² |
|---|---|---|---|---|
| 160 | H | H | *−CH₂CH₂−C₆H₄−C₂H₅ | *−CH₂CH₂−C₆H₄−C₂H₅ |
| 161 | H | H | *−CH₂CH₂−C₆H₄−C₆H₁₃ | *−CH₂CH₂−C₆H₄−C₆H₁₃ |
| 162 | H | H | *−CH₂CH₂−C₆H₄−C₁₀H₂₁ | *−CH₂CH₂−C₆H₄−C₁₀H₂₁ |
| 163 | H | H | *−CH₂CH₂−C₆H₅ | *−CH₂CH₂−C₆H₄−C₁₀H₄F₁₇ |
| 164 | H | H | *−CH₂CH₂−O−C(=O)−C(CH₃)=CH₂ | *−CH₂CH₂−O−C(=O)−C(CH₃)=CH₂ |
| 165 | H | H | *−CH₂−CH(OH)−CH₂OH | *−CH₂−CH(OH)−CH₂OH |
| 166 | Br | Br | *−CH₂CH₂−C₆H₅ | *−CH₂CH₂−C₆H₅ |
| 167 | CN | CN | *−CH₂CH₂−C₆H₅ | *−CH₂CH₂−C₆H₅ |
| 168 | *-(2-thienyl) | *-(2-thienyl) | *−CH₂CH₂−C₆H₅ | *−CH₂CH₂−C₆H₅ |
| 169 | *-(2-selenophenyl) | *-(2-selenophenyl) | *−CH₂CH₂−C₆H₅ | *−CH₂CH₂−C₆H₅ |

-continued
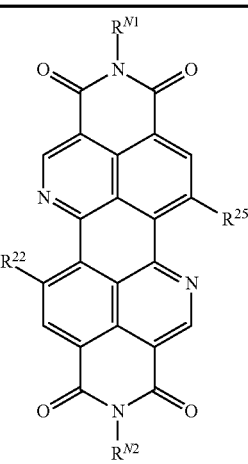
| No. | R²² | R²⁵ | RN¹ | RN² |
|---|---|---|---|---|
| 170 | 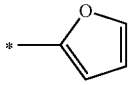 |  | 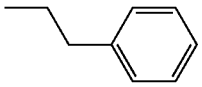 | 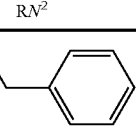 |
| 171 | CN | CN | *—$C_8H_{17}$ | *—$C_8H_{17}$ |
| 172 | F | F |  |  |
| 173 | H | H | 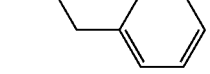 | 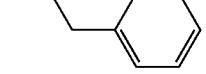 |
| 174 | H | H | *—$CH_2CH_2C_6F_{13}$ | 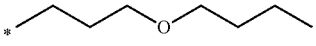 |
| 175 | H | H | 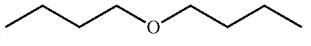 | 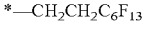 |
| 176 | H | H | 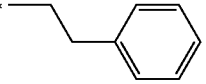 | 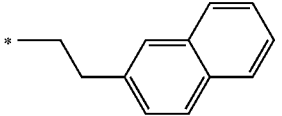 |
| 177 | H | H | 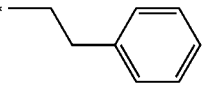 | 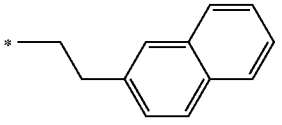 |
| 178 | H | H | 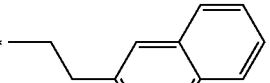 | 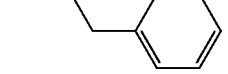 |
| 179 | H | H | 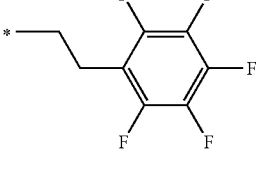 | 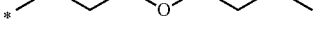 |
| 180 | H | H | 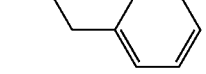 | 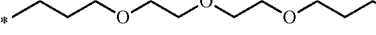 |

-continued

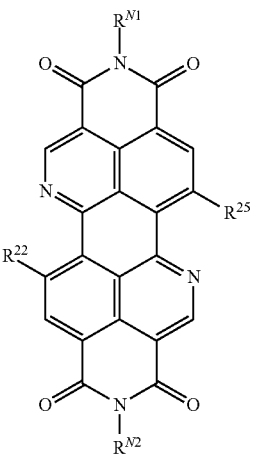

| No. | R²² | R²⁵ | RN¹ | RN² |
|---|---|---|---|---|
| 181 | H | H | *—CH₂CH(C₈H₁₇)C₁₀H₂₁ (2-octyldodecyl) | *—CH₂CH(C₈H₁₇)C₁₀H₂₁ |
| 182 | H | H | *—CH₂CH(C₈H₁₇)C₁₀H₂₁ | *—CH₂CH₂C₆H₅ |
| 183 | F | F | *—CH₂CH₂C₆F₁₃ | *—CH₂CH₂C₆H₅ |
| 184 | CN | CN | *—CH₂CH₂C₆F₁₃ | *—CH₂CH₂C₆H₅ |
| 185 | Cl | Cl | *—C₈H₁₇ | *—C₈H₁₇ |
| 186 | ON | ON | *—(S)-CH(CH₃)C₄H₉ | *—(S)-CH(CH₃)C₄H₉ |
| 186 | F | F | *—(S)-CH(CH₃)C₄H₉ | *—(S)-CH(CH₃)C₄H₉ |
| 187 | Cl | Cl | *—(S)-CH(CH₃)C₄H₉ | *—(S)-CH(CH₃)C₄H₉ |
| 188 | H | H | *—C₂H₅ | *—C₂H₅ |
| 189 | H | H | *—C₃H₇ | *—C₃H₇ |
| 190 | H | H | *—C₄H₉ | *—C₄H₉ |
| 191 | H | H | *—C₅H₁₁ | *—C₅H₁₁ |
| 192 | H | H | *—C₆H₁₃ | *—C₆H₁₃ |
| 193 | H | H | *—C₇H₁₅ | *—C₇H₁₅ |
| 194 | *-(thiazol-2-yl) | *-(thiazol-2-yl) | *—C₈H₁₇ | *—C₈H₁₇ |

-continued

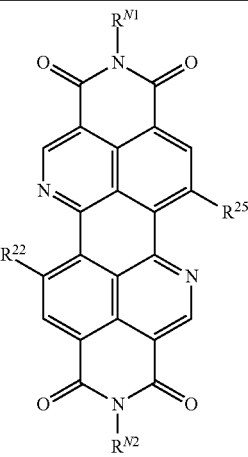

| No. | $R^{22}$ | $R^{25}$ | $R^{N1}$ | $R^{N2}$ |
|---|---|---|---|---|
| 195 | *-thiazol-5-yl | *-thiazol-5-yl | *—$C_8H_{17}$ | *—$C_8H_{17}$ |
| 196 | *—C≡CSiMe$_3$ | *—C≡CSiMe$_3$ | *—$C_8H_{17}$ | *—$C_8H_{17}$ |
| 197 | *—C≡CC$_6$H$_{13}$ | *—C≡CC$_6$H$_{13}$ | *—Me | *—Me |
| 198 | F | F | *—$C_8H_{17}$ | *—$C_8H_{17}$ |
| 199 | Br | Br | *—$C_8H_{17}$ | *—$C_8H_{17}$ |
| 200 | H | H | *—$C_5H_{11}$ | *—CH$_2$CH$_2$Ph |
| 201 | H | H | *—CH=CH—Ph | *—CH=CH—Ph |
| 202 | H | H | *—C≡C—Ph | *—C≡C—Ph |
| 203 | H | H | *—(CH$_2$)$_6$—OMe | *—(CH$_2$)$_6$—OMe |
| 204 | H | H | *—$C_8H_{17}$ | *—(CH$_2$)$_6$—OMe |
| 205 | ON | ON | *—$C_8H_{17}$ | *—(CH$_2$)$_6$—OMe |
| 206 | H | H | *—CH$_2$CF$_2$CF$_2$CF$_2$CF$_2$CH$_2$OMe | *—CH$_2$CF$_2$CF$_2$CF$_2$CF$_2$CH$_2$OMe |
| 207 | H | H | *—CH$_2$CH$_2$-cyclohexyl | *—CH$_2$CH$_2$-cyclohexyl |
| 208 | H | H | *—(CH$_2$)$_3$SiMe$_3$ | *—(CH$_2$)$_3$SiMe$_3$ |
| 209 | H | H | *—(CH$_2$)$_3$Si(i-Pr)$_3$ | *—(CH$_2$)$_3$Si(i-Pr)$_3$ |

-continued
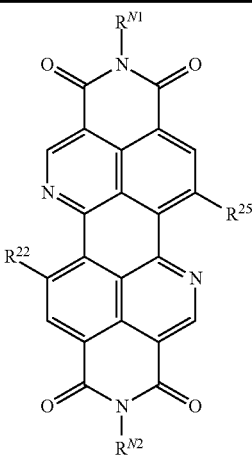
| No. | R22 | R25 | RN1 | RN2 |
|---|---|---|---|---|
| 210 | *-thiazol-2-yl | *-thiazol-2-yl | H | H |
| 211 | *—C≡CC6H13 | *—C≡CC6H13 | H | H |
| 212 | *—C8H17 | *—C8H17 | H | H |
| 213 | H | H | *—CH2CH(C6H5)2 | *—CH2CH(C6H5)2 |
| 214 | H | H | 3,7-dimethyloctyl | 3,7-dimethyloctyl |
| 215 | CN | CN | 3,7-dimethyloctyl | 3,7-dimethyloctyl |
| 216 | CN | CN | isobutyl | isobutyl |
| 217 | CN | CN | 2-methylpropyl | 2-methylpropyl |
| 218 | CN | CN | 2-ethylbutyl | 2-ethylbutyl |
| 219 | CN | CN | 3-methylbutyl | 3-methylbutyl |
| 220 | CF3 | CF3 | *—C8H17 | *—C8H17 |
| 221 | CN | CN | *—C8H17 | *—C8H17 |
| 222 | CF3 | CF3 | *—CH2CH2C6H5 | *—CH2CH2C6H5 |

-continued
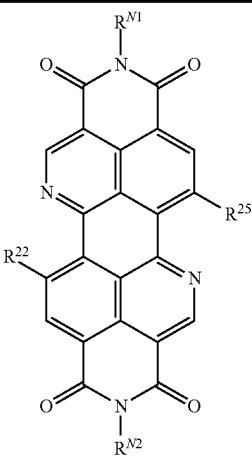
| No. | $R^{22}$ | $R^{25}$ | $R^{N1}$ | $R^{N2}$ |
|---|---|---|---|---|
| 223 | F | F | | |
| 224 | F | F | | |
| 225 | F | F | | |
| 226 | $CF_3$ | $CF_3$ | | |
| 227 | F | F | | |
| 228 | F | F | | |
| 229 | F | F | *—$(CH_2)_7$Ph | *—$(CH_2)_7$Ph |
| 230 | F | F | *—$(CH_2)_3$Ph | *—$(CH_2)_3$Ph |
| 231 | F | F | | |
| 232 | CN | CN | | |
The compounds shown in Nos. 233 to 262 are compounds having the following central structure.

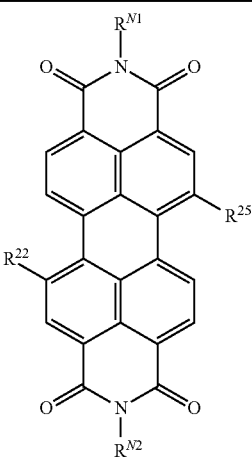

| No. | $R^{22}$ | $R^{25}$ | $R^{N1}$ | $R^{N2}$ |
|---|---|---|---|---|
| 233 | H | H | *-CH₂CH₂-(4-pyridyl) | *-CH₂CH₂-(4-pyridyl) |
| 234 | H | H | *-CH₂CH₂-(3-pyridyl) | *-CH₂CH₂-(3-pyridyl) |
| 235 | H | H | *-CH₂CH₂-(2-pyrimidinyl) | *-CH₂CH₂-(2-pyrimidinyl) |
| 236 | H | H | *-CH₂CH₂-(4-(1-C₁₀H₂₁-pyridinium)) I⁻ | *-CH₂CH₂-(4-(1-C₁₀H₂₁-pyridinium)) I⁻ |
| 237 | H | H | *-CH₂CH₂-C₆H₄-C₂H₅ | *-CH₂CH₂-C₆H₄-C₂H₅ |
| 238 | H | H | *-CH₂CH₂-C₆H₄-C₆H₁₃ | *-CH₂CH₂-C₆H₄-C₆H₁₃ |
| 239 | H | H | *-CH₂CH₂-C₆H₄-C₁₀H₂₁ | *-CH₂CH₂-C₆H₄-C₁₀H₂₁ |
| 240 | H | H | *-CH₂CH₂-C₆H₅ | *-CH₂CH₂-C₆H₄-C₁₀H₄F₁₇ |
| 241 | H | H | *-CH₂CH₂-O-C(O)-C(CH₃)=CH₂ | *-CH₂CH₂-O-C(O)-C(CH₃)=CH₂ |
| 242 | H | H | *-CH₂-CH(OH)-CH₂OH | *-CH₂-CH(OH)-CH₂OH |

-continued

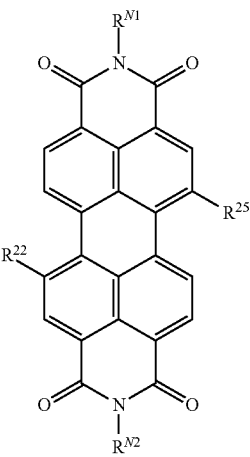

| No. | R²² | R²⁵ | R^{N1} | R^{N2} |
|---|---|---|---|---|
| 243 | Br | Br | *–CH₂CH₂–C₆H₅ | *–CH₂CH₂–C₆H₅ |
| 244 | CN | CN | *–CH₂CH₂–C₆H₅ | *–CH₂CH₂–C₆H₅ |
| 245 | *-(2-thienyl) | *-(2-thienyl) | *–CH₂CH₂–C₆H₅ | *–CH₂CH₂–C₆H₅ |
| 246 | *-(2-selenophenyl) | *-(2-selenophenyl) | *–CH₂CH₂–C₆H₅ | *–CH₂CH₂–C₆H₅ |
| 247 | *-(2-furyl) | *-(2-furyl) | *–CH₂CH₂–C₆H₅ | *–CH₂CH₂–C₆H₅ |
| 248 | CN | CN | *—C₈H₁₇ | *—C₈H₁₇ |
| 249 | F | F | *–CH₂CH₂–C₆H₅ | *–CH₂CH₂–C₆H₅ |
| 250 | H | H | *–(CH₂)₃–O–C₄H₉ | *–(CH₂)₃–O–C₄H₉ |
| 251 | H | H | *—CH₂CH₂C₆F₁₃ | *–CH₂CH₂–C₆H₅ |
| 252 | H | H | *–CH₂CH₂–(naphthyl) | *–CH₂CH₂–C₆H₅ |
| 253 | H | H | *–CH₂CH₂–(2-naphthyl) | *–CH₂CH₂–(2-naphthyl) |

-continued

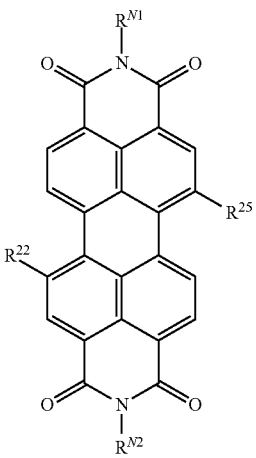

| No. | $R^{22}$ | $R^{25}$ | $R^{N1}$ | $R^{N2}$ |
|---|---|---|---|---|
| 254 | H | H | *-CH₂CH₂-phenyl | *-CH₂CH₂-C₆F₅ |
| 255 | H | H | *-(CH₂)₃-O-(CH₂)₃-CH₃ | *-CH₂CH₂-phenyl |
| 256 | H | H | *-(CH₂)₃-O-CH₂CH₂-O-CH₂CH₂-O-(CH₂)₂-CH₃ | *-(CH₂)₃-O-CH₂CH₂-O-CH₂CH₂-O-(CH₂)₂-CH₃ |
| 257 | H | H | *-(CH₂)₃-O-CH₂CH₂-O-CH₂CH₂-O-(CH₂)₂-CH₃ | *-CH₂CH₂-phenyl |
| 258 | H | H | 2-hexyldecyl | 2-hexyldecyl |
| 259 | H | H | 2-hexyldecyl | *-CH₂CH₂-phenyl |
| 260 | F | F | *—CH₂CH₂C₆F₁₃ | *-CH₂CH₂-phenyl |
| 261 | CN | CN | *—CH₂CH₂C₆F₁₃ | *-CH₂CH₂-phenyl |
| 262 | CN | CN | (S)-2-methylpentyl | (S)-2-methylpentyl |

51
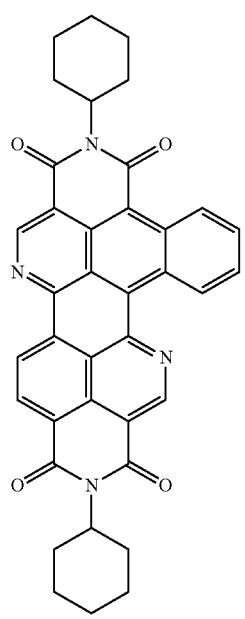
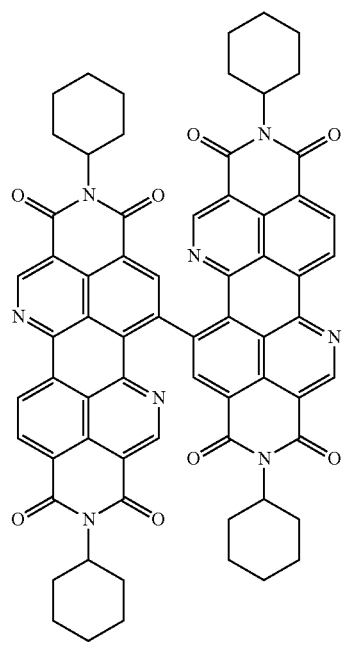
52
-continued
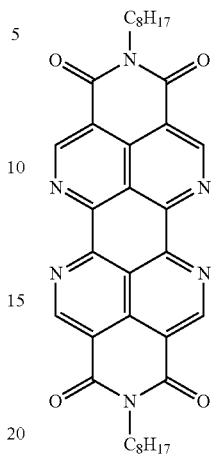 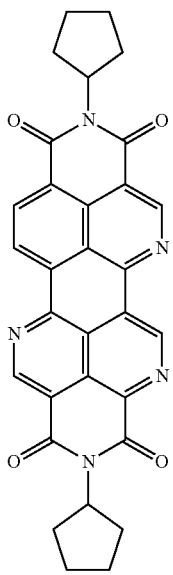
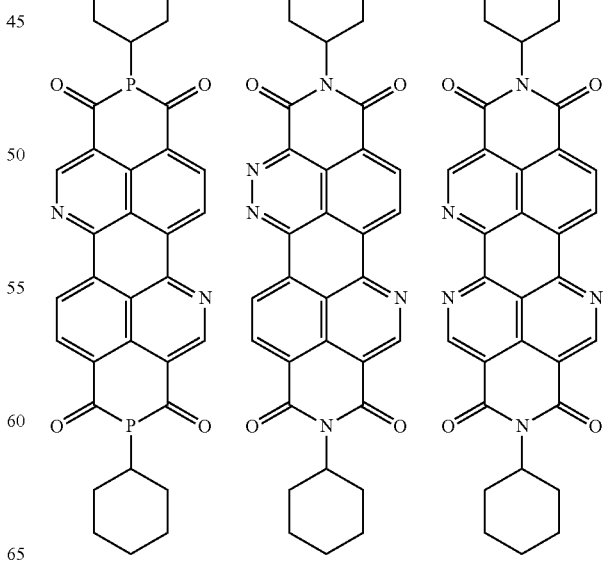

-continued

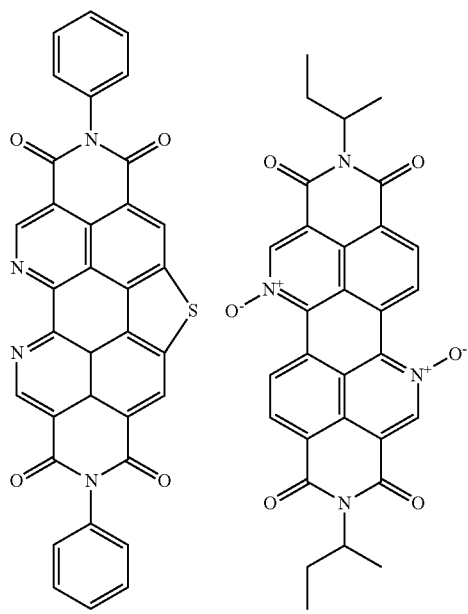

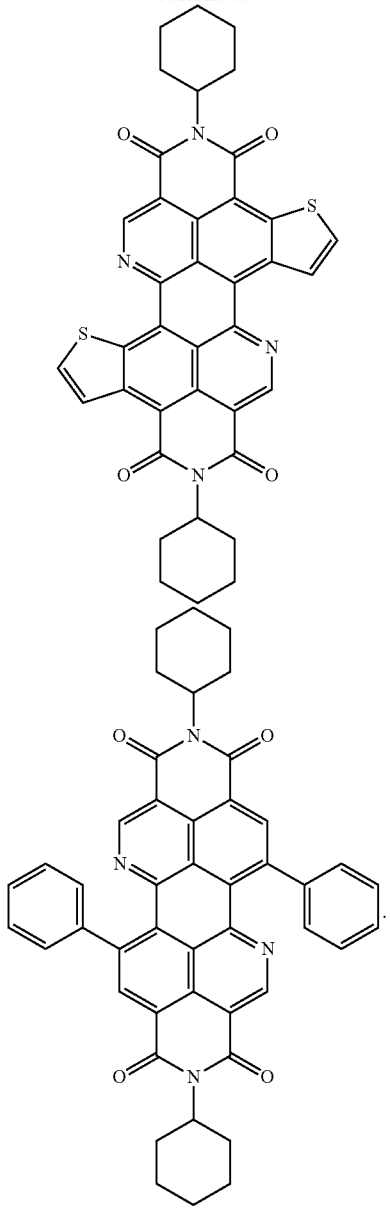

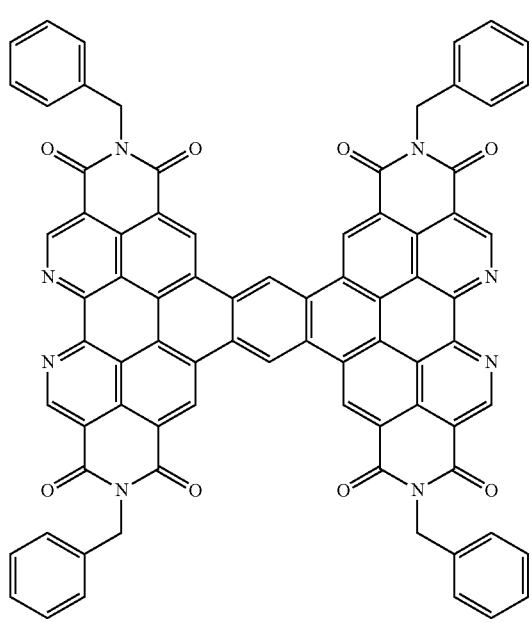

From the viewpoint of improvement in carrier mobility, durability, and material stability, the molecular weight of the specific compound is preferably 350 or more, more preferably 400 or more, and still more preferably 500 or more. In addition, from the viewpoint of solubility, the molecular weight is preferably 3,000 or less, more preferably 2,000 or less, and still more preferably 1,000 or less.

A method for synthesizing the specific compound is not particularly limited, and the specific compound can be synthesized with reference to a usual method. For example, the synthesis method of JP2018-6745A can be referred to.

The specific compound may be used alone, or in combination of two or more kinds thereof.

The content of the specific compound in the composition according to the embodiment of the present invention is preferably 10% by mass or more, more preferably 30% by mass or more, and still more preferably 50% by mass or more with respect to the total solid content. The upper limit thereof may be 100% by mass. In a case where the composition contains a binder polymer or the like described later, this upper limit is, for example, preferably 90% by mass or less and more preferably 80% by mass or less.

The solid content of the composition is intended as a component forming an organic semiconductor film described later, and does not include a solvent (for example, the alcohol represented by Formula (S1) and an organic solvent described later). In addition, even in a case where a component is liquid, the component is included in the solid content as long as the component forming the organic semiconductor film described later.

Alcohol Represented by Formula (S1)

The alcohol represented by Formula (S1) will be described.

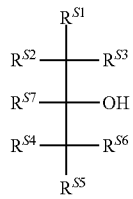

In Formula (S1), $R^{S1}$ to $R^{S6}$ each independently represent a hydrogen atom, a fluorine atom, or a substituent.

The above-described substituent which can be adopted as $R^{S1}$ to $R^{S6}$ is a substituent other than a fluorine atom, and examples thereof include a group other than a fluorine atom among the groups selected from the above-described substituent group Z. The group selected from the substituent group Z may further have a substituent. Examples of such a substituent include a group selected from the substituent group Z.

The above-described substituent which can be adopted as $R^{S1}$ to $R^{S6}$ is preferably a halogen atom other than a fluorine atom (preferably, a chlorine atom), an alkyl group, or an alkoxy group. Examples of the substituent which can be further included in the above-described alkyl group and the above-described alkoxy group include a halogen atom (preferably, a fluorine atom or a chlorine atom).

At least four of $R^{S1}$ to $R^{S6}$ are fluorine atoms, and it is preferable that four to six of $R^{S1}$ to $R^{S6}$ are fluorine atoms, it is more preferable that five or six of $R^{S1}$ to $R^{S6}$ are fluorine atoms, and it is still more preferable that all six of $R^{S1}$ to $R^{S6}$ are fluorine atoms.

In Formula (S1), $R^{S7}$ represents a hydrogen atom or a substituent.

Examples of the above-described substituent which can be adopted as $R^{S7}$ include the groups selected from the above-described substituent group Z (preferably, an alkyl group, an alkenyl group, an aryl group, a heterocyclic group, an acyl group, an alkoxycarbonyl group, a hydroxy group, a cyano group, or a carboxy group).

The group selected from the substituent group Z may further have a substituent. Examples of such a substituent include the groups selected from the above-described substituent group Z (preferably, an alkyl group, an alkenyl group, an aryl group, a heterocyclic group, an acyl group, an alkoxycarbonyl group, a hydroxy group, a cyano group, or a carboxy group).

As the above-described substituent which can be adopted as $R^{S7}$, a methyl group, a trifluoromethyl group, or a phenyl group is preferable.

The alcohol represented by Formula (S1) is preferably a compound represented by Formula (S2).

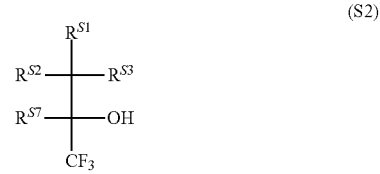

In Formula (S2), $R^{S1}$ to $R^{S3}$ each independently represent a hydrogen atom, a fluorine atom, or a substituent.

$R^{S7}$ represents a hydrogen atom or a substituent.

$R^{S1}$ to $R^{S3}$, and $R^{S7}$ in Formula (S2) are the same as $R^{S1}$ to $R^{S3}$, and $R^{S7}$ in Formula (S1).

However, at least one of $R^{S1}$, $R^{S2}$, or $R^{S3}$ is a fluorine atom, and it is preferable that one to three of $R^{S1}$ to $R^{S3}$ are fluorine atoms, it is more preferable that two or three of $R^{S1}$ to $R^{S3}$ are fluorine atoms, and it is still more preferable that all three of $R^{S1}$ to $R^{S3}$ are fluorine atoms.

The alcohol represented by Formula (S1) is more preferably a compound represented by Formula (S3).

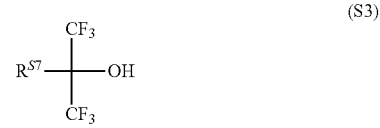

In Formula (S3), $R^{S7}$ represents a hydrogen atom or a substituent.

$R^{S7}$ in Formula (S3) is the same as $R^{S7}$ in Formula (S1).

The alcohol represented by Formula (S1) is preferably liquid at room temperature.

The standard boiling point of the alcohol represented by Formula (S1) is preferably 25° C. to 250° C. and more preferably 40° C. to 200° C.

Specific examples of the alcohol represented by Formula (S1) are shown below and Examples, but the present invention is not limited thereto.

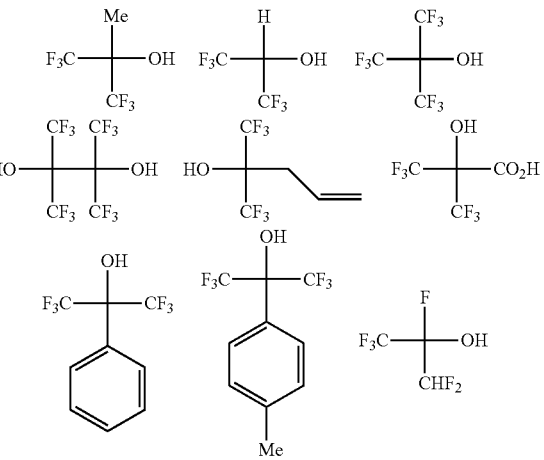

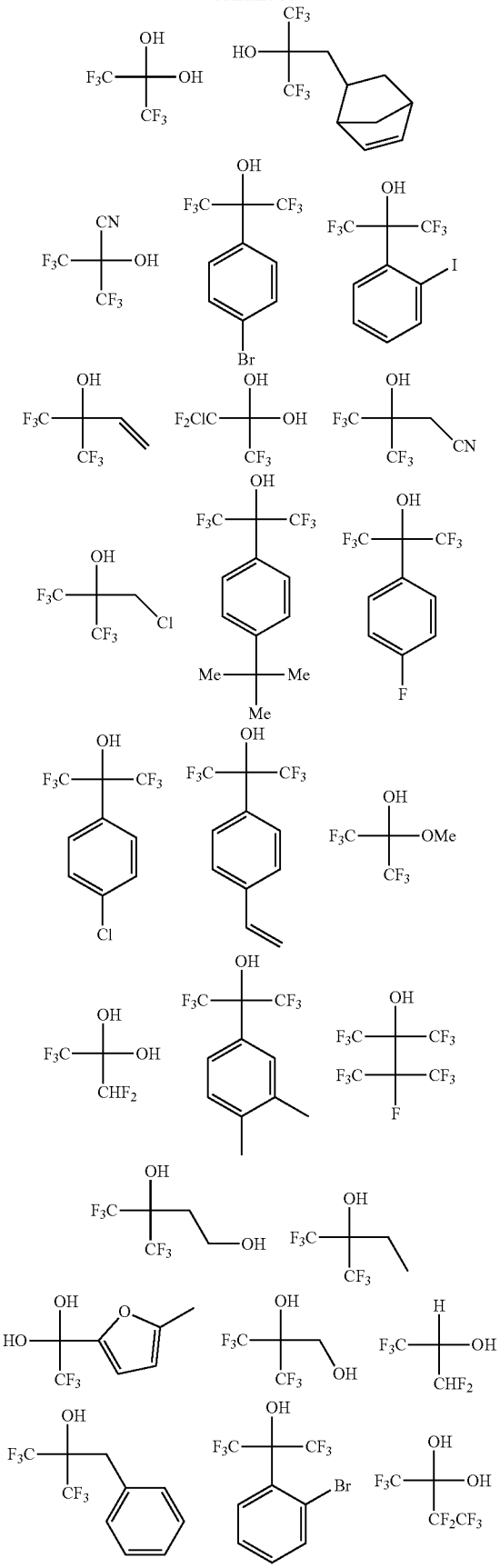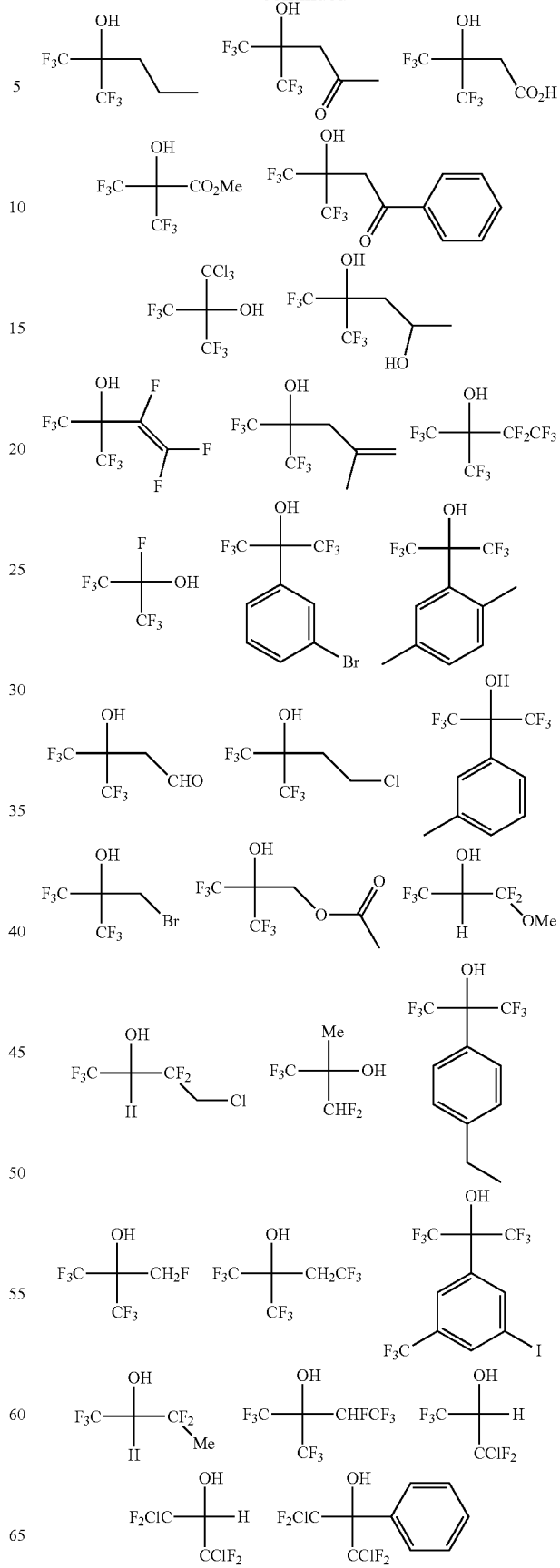

-continued

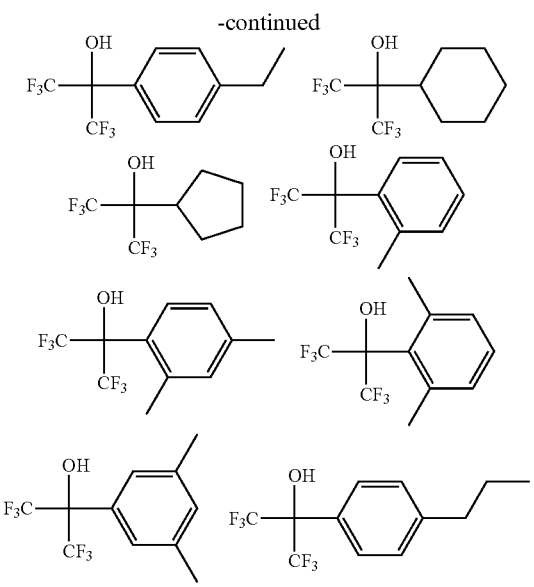

The alcohol represented by Formula (S1) may be used alone, or in combination of two or more kinds thereof.

The content of the alcohol represented by Formula (S1) in the composition according to the embodiment of the present invention is preferably 3% to 99.999% by mass, more preferably 5% to 99.999% by mass, and particularly preferably 10% to 99.999% by mass with respect to the total mass of the composition.

Organic Solvent

The composition according to the embodiment of the present invention preferably further contains an organic solvent.

The organic solvent herein is a compound other than the alcohol represented by Formula (S1).

In a case where the composition according to the embodiment of the present invention contains an organic solvent, it is considered that, at a location other than a location where the alcohol represented by Formula (51) is hydrogen-bonded to the specific compound, the organic solvent also interacts with the specific compound, thereby improving solubility of the specific compound in the composition.

The organic solvent is not particularly limited, and examples thereof include hydrocarbon solvents such as hexane, cyclohexane, octane, decane, toluene, xylene, mesitylene, ethylbenzene, amylbenzene, decalin, 1-methylnaphthalene, 1-ethylnaphthalene, 1,6-dimethylnaphthalene, and tetralin;

ketone solvents such as acetone, methyl ethyl ketone, methyl isobutyl ketone, cyclohexanone, acetophenone, propiophenone, isophorone, and butyrophenone;

halogenated hydrocarbon solvents such as dichloromethane, chloroform, tetrachloromethane, dichloroethane, trichloroethane, tetrachloroethane, chlorobenzene, 1,2-dichlorobenzene, 1,2,4-trichlorobenzene, chlorotoluene, 1-chloronaphthalene, and 1-fluoronaphthalene;

heterocyclic solvents such as pyridine, picoline, quinoline, thiophene, 3-butylthiophene, and thieno[2,3-b]thiophene;

halogenated heterocyclic solvents such as 2-chlorothiophene, 3-chlorothiophene, 2,5-dichlorothiophene, 3,4-dichlorothiophene, 2-bromothiophene, 3-bromothiophene, 2,3-dibromothiophene, 2,4-dibromothiophene, 2,5-dibromothiophene, 3,4-dibromothiophene, and 3,4-dichloro-1,2,5-thiadiazole;

ester solvents such as ethyl acetate, butyl acetate, amyl acetate, 2-ethylhexyl acetate, γ-butyrolactone, and phenyl acetate;

alcohol solvents such as methanol, propanol, butanol, pentanol, hexanol, cyclohexanol, methyl cellosolve, ethyl cellosolve, and ethylene glycol;

ether solvents such as dibutyl ether, tetrahydrofuran, dioxane, dimethoxyethane, anisole, ethoxybenzene, propoxybenzene, isopropoxybenzene, butoxybenzene, 2-methylanisole, 3-methylanisole, 4-methylanisole, 4-ethylanisole, dimethylanisole (any of 2,3-, 2,4-, 2,5-, 2,6-, 3,4-, 3,5-, and 3,6-), and 1,4-benzodioxane;

amide or imide solvents such as N,N-dimethylformamide, N,N-dimethylacetamide, 1-methyl-2-pyrrolidone, 1-methyl-2-imidazolidinone, and 1,3-dimethyl-2-imidazolidinone;

sulfoxide solvents such as dimethyl sulfoxide;

phosphate ester solvents such as trimethyl phosphate, and nitrile solvents such as acetonitrile and benzonitrile; and nitro solvents such as nitromethane and nitrobenzene.

Among these, the organic solvent is preferably a compound consisting of only one or more atoms selected from the group consisting of a carbon atom, a hydrogen atom, and a halogen atom.

In a case where the organic solvent is a compound consisting of only these atoms, it is considered that the improvement of the solubility of the specific compound can be promoted while maintaining the good hydrogen bond between the alcohol represented by Formula (S1) and the specific compound.

Among these, a hydrocarbon solvent or a halogenated hydrocarbon solvent is preferable, and toluene, ethylbenzene, xylene, mesitylene, chloroform, dichloromethane, tetrachloroethane, 1,2-dichlorobenzene, chlorobenzene, 1-methylnaphthalene, 1-chloronaphthalene, 1-fluoronaphthalene, 1,2,4-trichlorobenzene, 1-ethylnaphthalene, 1,6-dimethylnaphthalene, or tetralin is more preferable.

The content of the organic solvent in the composition according to the embodiment of the present invention is preferably 3% to 99.9% by mass and more preferably 5% to 99.5% by mass with respect to the total mass of the composition.

The organic solvent may be used alone, or in combination of two or more kinds thereof.

In the composition according to the embodiment of the present invention, the total content of the alcohol represented by Formula (S1) and the organic solvent is preferably 90% to 99.999% by mass, more preferably 95% to 99.999% by mass, and still more preferably 96% to 99.999% by mass with respect to the total mass of the composition.

In addition, in the composition according to the embodiment of the present invention, the content of the alcohol represented by Formula (S1) to the total content of the alcohol represented by Formula (S1) and the organic solvent is preferably 5% by volume or more and more preferably 10% by volume or more. The upper limit is 100% by volume or less, preferably 99% by volume or less, and more preferably 95% by volume or less.

Binder Polymer

The composition according to the embodiment of the present invention may contain a binder polymer. From the viewpoint that an organic semiconductor film having high film quality can be obtained, the composition preferably contains a binder polymer.

The type of the binder polymer is not particularly limited, and a known binder polymer can be used. Examples of the binder polymer include an insulating polymer including polystyrene, poly(α-methylstyrene), polycarbonate, polyarylate, polyester, polyamide, polyimide, polyurethane, polysiloxane, polysulfone, polymethyl methacrylate, polymethyl acrylate, cellulose, polyethylene, and polypropylene, and a copolymer thereof.

In addition to these, examples of the binder polymer include a rubber including an ethylene-propylene rubber, an acrylonitrile-butadiene rubber, a hydrogenated nitrile rubber, a fluoro-rubber, a perfluoro elastomer, a tetrafluoroethylene-propylene copolymer, an ethylene-propylene-diene copolymer, a styrene-butadiene rubber, polychloroprene, polyneoprene, a butyl rubber, a methylphenyl silicone resin, a methylphenylvinyl silicone resin, a methylvinyl silicone resin, a fluorosilicone resin, an acryl rubber, an ethylene acryl rubber, chlorosulfonated polyethylene, chloropolyethylene, an epichlorohydrin copolymer, a polyisoprene-natural rubber copolymer, a polyisoprene rubber, a styrene-isoprene block copolymer, a polyester-urethane copolymer, a polyether-urethane copolymer, a polyether ester thermoplastic elastomer, and a polybutadiene rubber, and a thermoplastic elastomer polymer.

Furthermore, examples of the binder polymer include a photoconductive polymer including polyvinylcarbazole and polysilane, a conductive polymer including polythiophene, polypyrrole, polyaniline, and poly p-phenylenevinylene, and a semiconductive polymer described in Chemistry of Materials, 2014, 26, p. 647.

In consideration of charge mobility, it is preferable that the binder polymer has a structure not including a polar group. Here, the polar group refers to a functional group having a heteroatom other than carbon atoms and hydrogen atoms. Since it has a structure not including a polar group, polystyrene or poly(α-methylstyrene) is preferable as the binder polymer. In addition, a semiconductive polymer is also preferable.

The glass transition temperature of the binder polymer is not particularly limited, and is appropriately set according to the use. For example, in a case of imparting firm mechanical strength to the organic semiconductor film, it is preferable that the glass transition temperature is set to be high. On the other hand, in a case of imparting flexibility to the organic semiconductor film, it is preferable that the glass transition temperature is set to be low.

The binder polymer may be used alone, or in combination of two or more kinds thereof.

In a case where the composition contains a binder polymer, from the viewpoint that the carrier mobility and durability of the organic semiconductor film in the organic thin film transistor are further improved, the content of the binder polymer in the composition is preferably 90% by mass or less and more preferably 70% by mass or less with respect to the total solid content of the composition. The lower limit thereof is not particularly limited, but is preferably 10% by mass or more and more preferably 20% by mass or more with respect to the total solid content of the composition.

The weight-average molecular weight of the binder polymer is not particularly limited, and is preferably 1,000 to 10,000,000, more preferably 3,000 to 5,000,000, and still more preferably 5,000 to 3,000,000. The weight-average molecular weight of the binder polymer can be obtained by gel permeation chromatography (GPC).

In the composition, the specific compound may be uniformly mixed with the binder polymer, or a part or all of the specific compound may be phase-separated from the binder polymer. From the viewpoint of ease of application or uniformity of application, it is preferable that the specific compound and the binder polymer are uniformly mixed at least in a case of application.

Other Components

The composition may contain a component other than the above-described components. Examples of such a component include various additives.

As the additive, an additive usually used in the composition can be used, and more specific examples thereof include a surfactant, an antioxidant, a crystallization control agent, and a crystal alignment control agent. As the surfactant and the antioxidant, paragraphs 0136 and 0137 of JP2015-195362A can be incorporated, and the contents thereof are incorporated in the present specification.

The additive may be used alone, or in combination of two or more kinds thereof.

The content of the additive in the composition is not particularly limited, but from the viewpoint that film forming properties are excellent and the carrier mobility and heat resistance are further improved, the content thereof is preferably 10% by mass or less, more preferably 5% by mass or less, and still more preferably 1% by mass or less with respect to the total solid content of the composition.

From the viewpoint of high water resistance, the viscosity of the composition is preferably 10 mPa·s or more.

Preparation Method

A method for preparing the composition is not particularly limited, and a usual preparation method can be adopted. For example, it is possible to prepare the composition by adding respective components in a predetermined amount to the alcohol represented by Formula (S1) and/or the organic solvent and stirring the mixture appropriately.

The respective components can be heated during or after stirring as necessary. The heating temperature is not particularly limited, and is determined, for example, in a range of 40° C. to 150° C. In a case of using the solvent, the heating temperature is determined to be a temperature in the above-described range and lower than the boiling point of the solvent.

However, in the composition according to the embodiment of the present invention, since the alcohol represented by Formula (S1), and a mixed solution of the alcohol and the organic solvent added as desired dissolve the specific compound well, in many cases, the composition can be produced without heating (lower than 40° C.).

In addition, as described above, since the composition according to the embodiment of the present invention dissolves the specific compound represented by Formula (1) well even at room temperature, in a case where the composition does not substantially contain the binder polymer, the purity of the specific compound represented by Formula (1) can be easily measured by analysis using liquid chromatography or the like.

For example, in a case where the composition is analyzed by liquid chromatography and the detection wavelength is set as 254 nm, the area ratio of a peak derived from the specific compound to the total peak surface area is preferably 95% or more and more preferably 99% or more.

Organic Thin Film Transistor

The composition according to the embodiment of the present invention is preferably used as a composition for forming an organic semiconductor layer, and more preferably used as a composition for forming an organic semiconductor layer for an organic thin film transistor.

Hereinafter, an organic thin film transistor (hereinafter, also described as an "organic TFT") which can be manufactured using the composition according to the embodiment of the present invention will be described.

The organic TFT includes an organic semiconductor film described later. As a result, the organic TFT exhibits high carrier mobility and can effectively suppress a decrease over time even in the atmosphere, thereby driving stably. The ambient temperature and humidity in the atmosphere is not particularly limited as long as a temperature or humidity in the use environment of the organic TFT, and examples thereof include room temperature (20° C.) as a temperature and 10 to 90 RH % as a humidity.

The organic TFT is preferably used as an organic field effect transistor (FET) and more preferably used as an insulated gate type FET in which the gate and the channel are insulated.

The thickness of the organic TFT is not particularly limited, but in a case of a thinner transistor, for example, the thickness of the entire organic TFT is preferably 0.1 to 0.5 µm.

The organic TFT includes an organic semiconductor film (also referred to as an organic semiconductor layer or a semiconductor active layer) including the specific compound, and can further include a source electrode, a drain electrode, a gate electrode, and a gate insulating film.

It is preferable that the organic TFT includes a gate electrode, an organic semiconductor film, a gate insulating film provided between the gate electrode and the organic semiconductor film, and a source electrode and a drain electrode which are provided in contact with the organic semiconductor film and are linked to each other through the organic semiconductor film, on a substrate. In the organic TFT, the organic semiconductor film and the gate insulating film are provided to be adjacent to each other.

The structure of the organic TFT is not particularly limited as long as the above-described respective layers are provided. For example, the organic TFT may have any structures of a bottom gate-bottom contact type, a top gate-bottom contact type, a bottom gate-top contact type, or a top gate-top contact type. The organic TFT is preferably a bottom gate type (bottom gate-bottom contact type or bottom gate-top contact type) in which the gate electrode is provided between the substrate and the organic semiconductor film.

Hereinafter, an example of the organic TFT will be described with reference to the drawings.

Bottom Gate-Bottom Contact Type Organic TFT

FIG. 1 is a schematic cross-sectional view showing a structure of a bottom gate-bottom contact type organic TFT 10 which is an example of the organic TFT.

As illustrated in FIG. 1, the organic TFT 10 has a substrate (base material) 1, a gate electrode 2, a gate insulating film 3, a source electrode 4A and a drain electrode 4B, an organic semiconductor film 5, and a sealing layer 6, in this order.

Hereinafter, a substrate (base material), a gate electrode, a gate insulating film, a source electrode, a drain electrode, an organic semiconductor film, a sealing layer, and a production method thereof will be described in detail.

Substrate

The substrate acts as supporting the gate electrode, the source electrode, the drain electrode, and other layers.

The type of the substrate is not particularly limited, and examples thereof include a plastic substrate, a silicon substrate, a glass substrate, and a ceramic substrate. Among these, from the viewpoint of applicability to each device and costs, a glass substrate or a plastic substrate is preferable.

The thickness of the substrate is not particularly limited. The upper limit of the thickness of the substrate is preferably 10 mm or less, more preferably 2 mm or less, and still more preferably 1.5 mm or less. The lower limit of the thickness of the substrate is preferably 0.01 mm or more and more preferably 0.05 mm or more.

Gate Electrode

As the gate electrode, an electrode which is usually used as a gate electrode of an organic TFT can be applied without particular limitation.

A material (electrode material) for forming the gate electrode is not particularly limited, and examples thereof include metals including gold, silver, aluminum, copper, chromium, nickel, cobalt, titanium, platinum, magnesium, calcium, barium, and sodium; conductive oxides including $InO_2$, $SnO_2$, and/or indium tin oxide (ITO); conductive polymers including polyaniline, polypyrrole, polythiophene, polyacetylene, and polydiacetylene; semiconductors including silicon, germanium, and gallium arsenide; and carbon materials including fullerene, carbon nanotube, and graphite. Among these, the above-described metals are preferable, and silver or aluminum is more preferable.

The thickness of the gate electrode is not particularly limited, but is preferably 20 to 200 nm.

The gate electrode may be a gate electrode which functions as the substrate, and in this case, the above-described substrate may not be provided.

The method of forming the gate electrode is not particularly limited, and examples thereof include a method of performing vacuum deposition (hereinafter, simply referred to as "vapor deposition") of or sputtering the above-described electrode material on the substrate, and a method of applying or printing a composition for forming an electrode, which contains the above-described electrode material, on the substrate. In addition, in a case of patterning the gate electrode, examples of the patterning method include printing methods including inkjet printing, screen printing, offset printing, and relief printing (flexographic printing), a photolithography method, and a mask vapor deposition method.

Gate Insulating Film

The gate insulating film is not particularly limited as long as the gate insulating film is a layer having insulating properties, and may be a single layer or a multilayer.

The material for forming the gate insulating film is not particularly limited, and examples thereof include polymers including polymethyl methacrylate, polystyrene, polyvinyl phenol, melamine resin, polyimide, polycarbonate, polyester, polyvinyl alcohol, polyvinyl acetate, polyurethane, polysulfone, polybenzoxazole, polysilsesquioxane, epoxy resin, and phenol resin; inorganic oxides including silicon dioxide, aluminum oxide, and titanium oxide; and nitrides including silicon nitride. Among these, from the viewpoint of compatibility with the organic semiconductor film, the above-described polymers are preferable, and from the viewpoint of uniformity of the film, the above-described inorganic oxides are preferable and silicon dioxide is more preferable.

These materials may be used singly, and two or more kinds thereof may be used in combination.

The film thickness of the gate insulating film is not particularly limited, but is preferably 100 to 1,000 nm.

The method of forming the gate insulating film is not particularly limited, and examples thereof include a method of applying a composition for forming a gate insulating film, which contains the above-described material, on the substrate on which the gate electrode is formed, and a method of performing vapor deposition of or sputtering the above-described material.

Source Electrode and Drain Electrode

In the organic TFT, the source electrode is an electrode in which a current flows from the outside through a wiring. In addition, the drain electrode is an electrode in which a current is sent to the outside through a wiring.

As materials for forming the source electrode and the drain electrode, the same material as the electrode material for forming the above-described gate electrode can be used. Among them, metal is preferable, and gold or silver is more preferable.

The thicknesses of the source electrode and the drain electrode are not particularly limited, but are respectively preferably 1 nm or more and more preferably 10 nm or more. In addition, the upper limit of the thicknesses of the source electrode and the drain electrode is preferably 500 nm or less and more preferably 300 nm or less.

The distance (gate length L) between the source electrode and the drain electrode may be appropriately determined, but the distance is preferably 200 µm or less and more preferably 100 µm or less. In addition, the gate width W may be appropriately determined, but the gate width W is preferably 5,000 µm or less and more preferably 1,000 µm or less. A ratio of the gate width W to the gate length L is not particularly limited, but for example, the ratio W/L is preferably 10 or more and more preferably 20 or more.

The method of forming the source electrode and the drain electrode is not particularly limited, and examples thereof include a method of performing vacuum deposition of or sputtering the electrode material on the substrate on which the gate electrode and the gate insulating film are formed, and a method of applying or printing a composition for forming an electrode on the substrate. In a case of patterning the source electrode and the drain electrode, the patterning method is the same as the method of the gate electrode described above.

Organic Semiconductor Film

Among these, the organic semiconductor film is preferably used as an organic semiconductor film of an organic thin film transistor. Hereinafter, a case where the organic semiconductor film of the present invention is used as an organic semiconductor film of an organic thin film transistor will be described.

As the organic semiconductor film in the organic TFT, an organic semiconductor film containing the specific compound is used. The specific compound contained in the organic semiconductor film may be one kind or two or more kinds.

In a case where the organic semiconductor film contains the specific compound, the carrier mobility of the organic semiconductor film can be improved, and the high carrier mobility can be maintained even in a case of being used or stored (left) in the atmosphere. The reason is not clear, but it is considered that the orbital energy of the lowest unoccupied molecular orbital of the specific compound is low.

The content of the specific compound in the organic semiconductor film can be appropriately set without particular limitation. For example, the content of the specific compound with respect to the total mass of the organic semiconductor film is preferably 10% by mass or more, more preferably 30% by mass or more, still more preferably 50% by mass or more. The upper limit thereof is not particularly limited, and the content of the specific compound with respect to the total mass of the organic semiconductor film may be 100% by mass. In a case where the organic semiconductor film contains the binder polymer or other components, the upper limit of the content of the specific compound with respect to the total mass of the organic semiconductor film is preferably 90% by mass or less and more preferably 80% by mass or less.

The organic semiconductor film may contain the above-described binder polymer, in addition to the specific compound. The binder polymer may be alone, or in combination of two or more kinds thereof.

In the organic semiconductor film, a contained state of the specific compound and the binder polymer contained is not particularly limited, but from the viewpoint of carrier mobility, it is preferable that the specific compound and the binder polymer are phase-separated from each other along a film thickness direction.

The content of the binder polymer in the organic semiconductor film can be appropriately set without particular limitation. In a case where the organic semiconductor film contains the binder polymer, the content of the binder polymer with respect to the total mass of the organic semiconductor film is preferably 90% by mass or less and more preferably 70% by mass or less. The lower limit thereof is not particularly limited, and the content of the binder polymer with respect to the total mass of the organic semiconductor film may be 0% by mass or more, preferably 10% by mass or more, and more preferably 20% by mass or more.

The organic semiconductor film may contain the above-described additive, in addition to the specific compound. The additive may be used alone, or in combination of two or more kinds thereof.

In a case where the organic semiconductor film contains the additive, the content of the additive with respect to the total mass of the organic semiconductor film is preferably 10% by mass or less, more preferably 5% by mass or less, and still more preferably 1% by mass or less.

The film thickness of the organic semiconductor film is appropriately determined depending on the organic TFT to be applied, but is preferably 10 to 500 nm, more preferably 20 to 200 nm.

This organic semiconductor film can be formed by applying the above-described composition. Details of a method for forming the organic semiconductor film will be described later.

The use of the organic semiconductor film containing the specific compound is not limited to the organic semiconductor film for the organic TFT, and the organic semiconductor film can be used as an organic semiconductor film included in each of the above-described organic semiconductor devices.

Sealing Layer

Since the organic TFT provided with the above-described organic semiconductor film is stably driven even in the atmosphere, it is not necessary to seal the entire organic TFT and block either the atmosphere (oxygen gas) or moisture, but for the purpose of stable driving for a longer period of time, the entire organic TFT may be sealed with a metal sealing can, or a sealing layer may be formed using a sealing agent.

As the sealing layer, a sealing agent (composition for forming a sealing layer) usually used for an organic TFT can be used. Examples of the sealing agent include inorganic materials including glass and silicon nitride, polymer materials including parylene, and low molecular weight materials.

The sealing layer can be formed by a usual method such as coating and drying, using the above-described sealing agent.

The thickness of the sealing layer is not particularly limited, but is preferably 0.2 to 10 μm.

Bottom Gate-Top Contact Type Organic TFT

Figure 2:
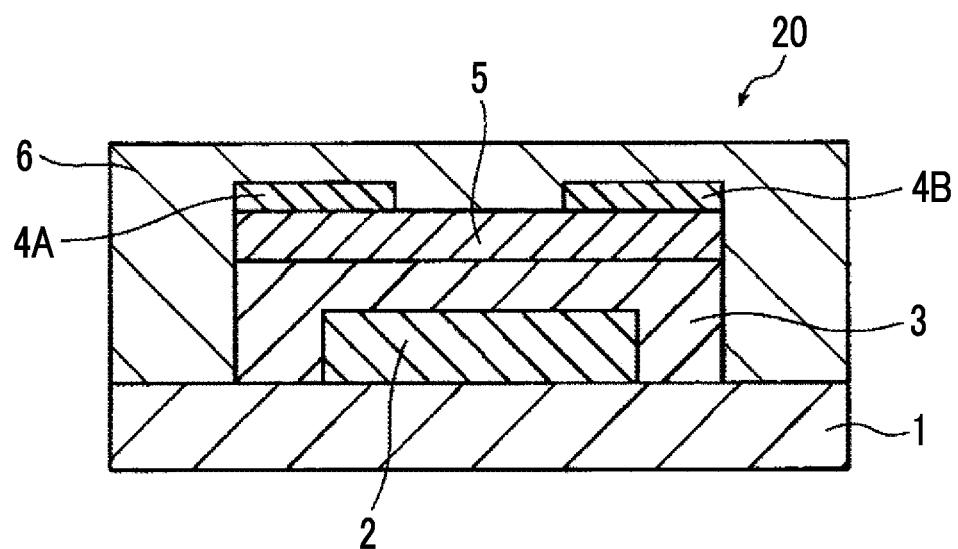
FIG. 2 is a schematic cross-sectional view showing a structure of a bottom gate-top contact type organic thin film transistor which is another example of the organic thin film transistor.

FIG. 2 is a schematic cross-sectional view showing a structure of a bottom gate-top contact type organic TFT 20 which is an example of the organic TFT.

As illustrated in FIG. 2, the organic TFT 20 has a substrate 1, a gate electrode 2, a gate insulating film 3, an organic semiconductor film 5, a source electrode 4A and a drain electrode 4B, and a sealing layer 6, in this order.

The organic TFT 20 is the same as the organic TFT 10, except that the layer configuration (lamination aspect) is different. Accordingly, the substrate, the gate electrode, the gate insulating film, the source electrode, the drain electrode, the organic semiconductor film, and the sealing layer are the same as those of the bottom gate-bottom contact type organic TFT, and thus descriptions thereof will be omitted.

Manufacturing Method of Organic TFT

A manufacturing method of the organic TFT is not particularly limited as long as the method includes a step of coating the substrate with the composition to form an organic semiconductor film.

The gate electrode, the gate insulating film, the source electrode, the drain electrode, and the sealing layer can all be produced or formed by the method described above.

Hereinafter, the step of forming the organic semiconductor film will be described.

In this step, the above-described composition is used.

In the present invention, the "coating the substrate with the composition" includes an aspect of applying the composition over the substrate through another layer provided on the substrate, in addition to an aspect of directly applying the composition to the substrate. Another layer (a layer which is in contact with the organic semiconductor film and is a base of the organic semiconductor film) to be coated with the composition is inevitably determined according to the structure of the organic TFT. For example, in a case where the organic TFT is a bottom gate type, the composition is applied at least to the surface of the gate insulating film.

In a case of forming the organic semiconductor film, the substrate may be heated or cooled. By changing the temperature of the substrate, it is possible to control packing of the specific compound in the film.

The temperature of the substrate is not particularly limited. For example, the temperature of the substrate is preferably set a range of 0° C. to 200° C., more preferably in a range of 10° C. to 150° C., and still more preferably in a range of 15° C. to 40° C.

By using the composition according to the embodiment of the present invention, even in a case where the temperature of the substrate is within the temperature range of around room temperature, the packing of the specific compound in the film is good.

A method of forming the organic semiconductor film using the composition according to the embodiment of the present invention is usually a so-called solution process.

The specific compound is stable even in the atmosphere. Therefore, the solution process can be performed in the atmosphere, and the composition can be applied over a large area.

As a method for applying the composition in the solution process, a usual method can be used. Examples thereof include coating methods including a drop casting method, a casting method, a dip coating method, a die coater method, a roll coater method, a bar coater method, and a spin coating method; various printing methods including an inkjet method, a screen printing method, a gravure printing method, a flexography printing method, an offset printing method, and a microcontact printing method; and a Langmuir-Blodgett (LB) method. Among these, a drop casting method, a casting method, a spin coating method, an inkjet method, a gravure printing method, a flexography printing method, an offset printing method, or a microcontact printing method is preferable.

As a method for applying the composition in the preferred aspect of the solution process described later, an inkjet method, a gravure printing method, a flexography printing method, an offset printing method, or a microcontact printing method is preferable, and a flexography printing method, a microcontact printing method, or an inkjet method is more preferable.

In the solution process, it is preferable to dry the composition coated on the substrate, and it is more preferable to perform the drying gradually. By drying the composition coated on the substrate, crystals of the specific compound can be precipitated to form the organic semiconductor film.

From the viewpoint of film quality, as a method for drying the composition, it is preferable that the composition is naturally dried or dried by heating on a heated substrate and then dried under reduced pressure. The temperature of the substrate during natural drying or heat drying is not limited because it is appropriately changed depending on the boiling point of the solvent in the composition, but for example, the temperature is preferably 10° C. to 200° C. and more preferably 15° C. to 150° C. The time for natural drying or heat drying is preferably 0.5 to 20 hours and more preferably 1 to 10 hours.

The temperature of the substrate during drying under reduced pressure is preferably 10° C. to 150° C. and more preferably 15° C. to 100° C. The time for drying under reduced pressure is preferably 1 to 20 hours and more preferably 2 to 10 hours. The pressure during drying under reduced pressure is preferably $10^{-6}$ to $9.9 \times 10^4$ Pa and more preferably $10^{-5}$ to $10^4$ Pa.

The composition dried as described above may be shaped into a predetermined shape or a pattern shape as necessary.

Aspect of Solution Process

Hereinafter, preferred aspects of the solution process will be described with reference to the drawings, but the solution process is not limited to the following aspects.

Examples of one aspect of the solution process include a method in which the composition (hereinafter, also referred to as a "coating liquid") is dropped (applied) to a part of a surface of the substrate to be in contact with the substrate and a member (hereinafter, simply referred to as a "member") disposed on the substrate, and then the dropped coating liquid is dried. The substrate and member used in this aspect will be described later.

In this aspect, the member maintains a state of being in contact with the substrate, or is not fixed to the substrate and maintains a constant distance from the substrate.

As long as the substrate and the member maintain the above-described state, in a case where the coating liquid is dropped or dried, the relative positional relationship between the substrate and the member may be fixed or changed. From the viewpoint of production efficiency, it is preferable to move the member with respect to the substrate to change the relative positional relationship between the substrate and the member. In addition, from the viewpoint of film quality and crystal size of the obtained organic semiconductor film, it is preferable that the member is stationary with respect to the substrate to fix the relative positional relationship between the substrate and the member.

A method of dropping the coating liquid in this aspect is not particularly limited. From the viewpoint that the thickness of the film of the coating liquid on the substrate tends to be thin and the drying easily proceeds from the edge of the film of the coating liquid, in a case of dropping the coating liquid, it is preferable to drop one drop of the coating liquid, or it is preferable to drop one drop at a time in a case where two or more drops are dropped. In a case of dropping the coating liquid, the volume of one drop of the coating liquid is preferably 0.01 to 0.2 mL and more preferably 0.02 to 0.1 mL.

By dropping the coating liquid onto a part of the surface of the substrate, to be in contact with both the substrate and the member, the thickness of the film of the coating liquid at the edge can be reduced.

The contact angle (25°) of the coating liquid with respect to the substrate is not particularly limited, but is preferably 0° to 90° and more preferably 10° to 20°. The contact angle of the coating liquid with respect to the substrate can be obtained by measuring an angle between the liquid droplet after 1 second has passed by dropping the coating liquid, and the substrate. Specifically, the liquid volume is set to 1.0 µL or more, and the static contact angle is measured by a liquid droplet method using a Teflon (registered trademark) needle. In this way, different substrates obtained by the same treatment are measured a plurality of times (usually, 5 times), and an average value thereof is calculated used as the contact angle.

The coating liquid preferably forms a meniscus with respect to the member, and more preferably forms a concave meniscus with respect to the member in terms of film quality.

Figure 3:
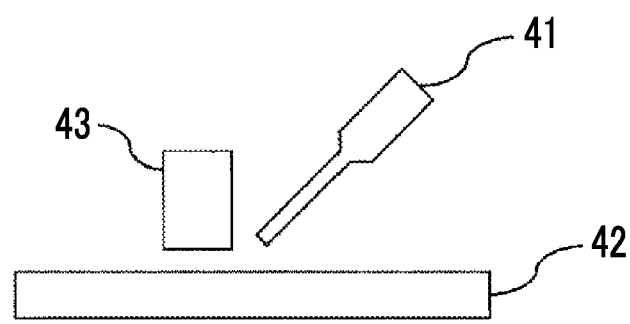
FIG. 3 is a schematic view showing an example of a method of forming an organic semiconductor film of the organic thin film transistor.
Figure 3:
Figure 3:
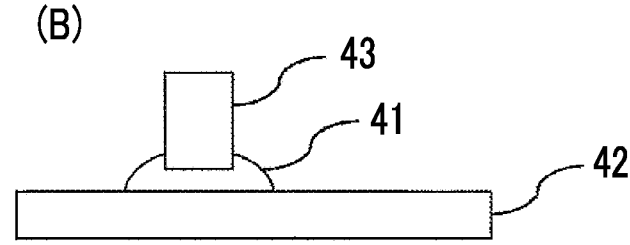
Figure 3:
Figure 3:
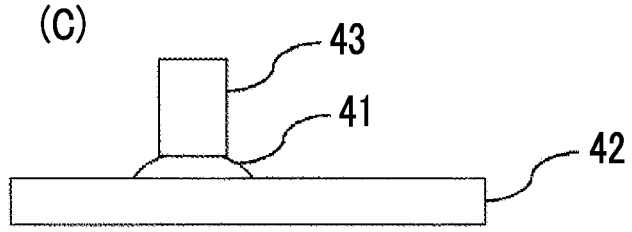

Hereinafter, a method of applying the coating liquid while maintaining a constant distance between the substrate and the member in this aspect will be described with reference to FIG. 3. FIG. 3 is a schematic view showing an example of the method of forming an organic semiconductor film of the organic TFT.

In this method, first, the substrate 42 and the member 43 are arranged at predetermined positions. Specifically, before dropping a coating liquid 41 onto the substrate, each of the substrate 42 and the member 43 is arranged at the position shown in (A) of FIG. 3. In this case, the distance between the substrate 42 and the member 43 which is not in contact with the substrate 42 is kept constant. The distance between the substrate 42 and the member 43 cannot be unconditionally determined because it varies depending on the coating amount, viscosity, and the like of the coating liquid, but can be appropriately set.

Next, as shown in (B) of FIG. 3, the coating liquid 41 is dropped onto a part (near a facing portion between the substrate 42 and the member 43) of the surface of the substrate 42, to be in contact with both the substrate 42 and the member 43.

Thereafter, the coating liquid 41 is dried while the relative positional relationship between the substrate 42 and the member 43 is fixed ((C) of FIG. 3). The drying method is not particularly limited, but the above-described method for drying the composition is preferable. As a result, the coating liquid 41 dries inward from both edges (ends) having a thin film thickness on the substrate 42, and the specific compound is crystallized. As a result, the specific compound can be arranged at a predetermined position as a crystal having a large size.

After the coating liquid 41 is dried, for example, the member 43 is pulled away from the substrate 42 by pulling up the member 43 perpendicularly to the main surface of the substrate 42. As a result, an organic semiconductor film having good film quality can be formed without leaving a trace of the member 43 on the formed crystals.

In this way, an organic semiconductor film formed of crystals of the specific compound can be formed.

Figure 4:
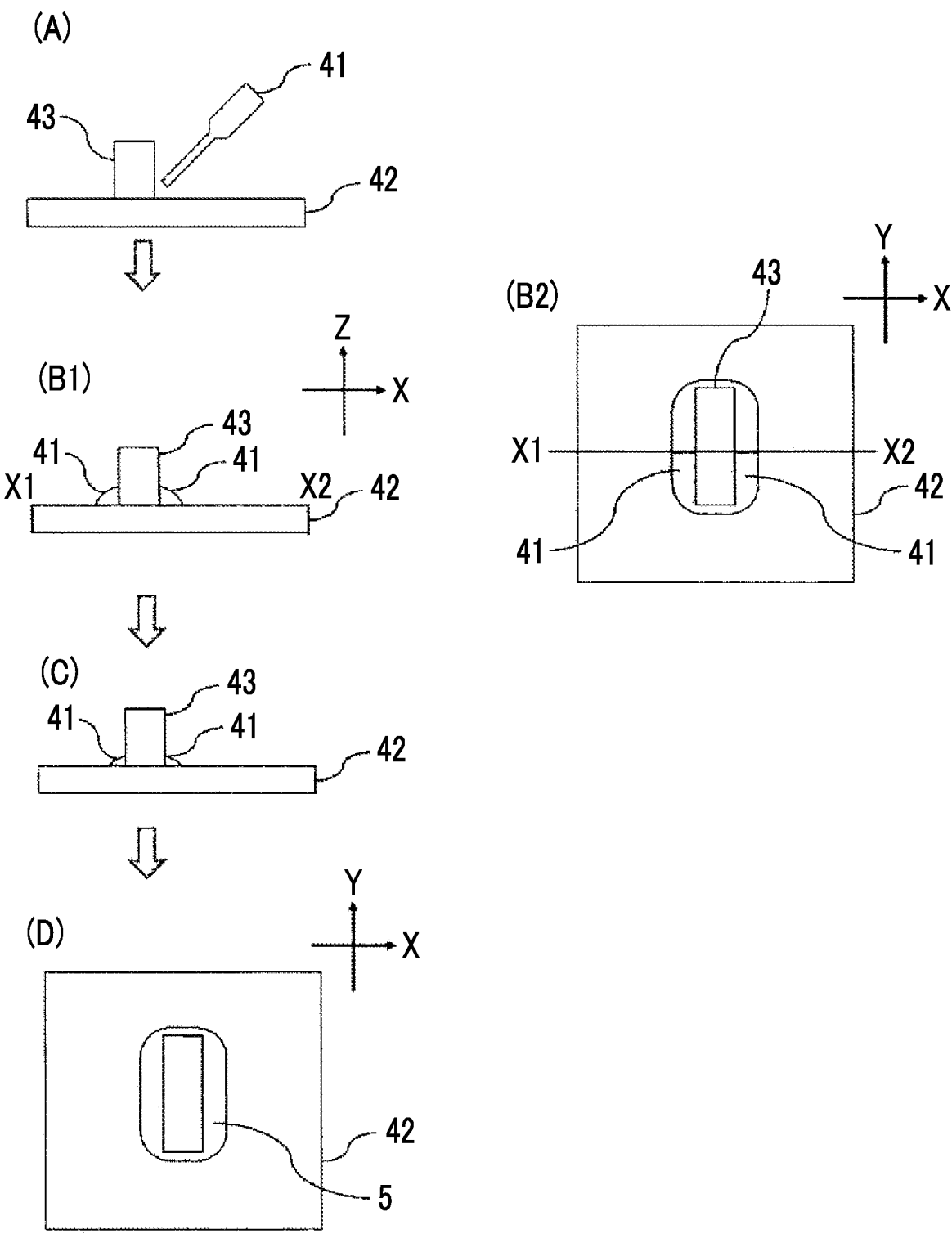
FIG. 4 is a schematic view showing still another example of the method of forming an organic semiconductor film of the organic thin film transistor.

Hereinafter, a method of applying the coating liquid in a state in which the substrate and the member are in contact with each other in this aspect will be described with reference to FIG. 4. FIG. 4 is a schematic view showing another example of the method of forming an organic semiconductor film of the organic TFT.

In this method, first, the substrate 42 and the member 43 are arranged in contact with each other. Specifically, before dropping a coating liquid 41 onto the substrate 42, each of the substrate 42 and the member 43 is arranged at the position shown in (A) of FIG. 4.

Next, as shown in (B1) of FIGS. 4 and (B2) of FIG. 4, the coating liquid 41 is dropped onto a part (near a contact portion between the substrate 42 and the member 43) of the surface of the substrate 42, to be in contact with both the substrate 42 and the member 43. In this case, as shown in (B2) of FIG. 4, it is preferable that the coating liquid 41 surrounds the contact portion between the substrate 42 and the member 43. (B1) of FIG. 4 is a front view of the substrate coated with the coating liquid, and (B2) of FIG. 4 is a plan view of the substrate coated with the coating liquid. Three-dimensional coordinates (X, Y, Z) are indicated in (B1) of FIGS. 4 and (B2) of FIG. 4.

Thereafter, the coating liquid 41 is dried while the relative positional relationship between the substrate 42 and the member 43 is fixed, preferably as described above ((C) of FIG. 4). The drying method is not particularly limited, but the above-described method for drying the composition is preferable. As a result, the coating liquid 41 dries inward from both ends having a thin film thickness on the substrate 42, and the specific compound is crystallized. As a result, the specific compound can be arranged at a predetermined position as a crystal having a large size.

After the coating liquid 41 is dried, for example, the member 43 is pulled away from the substrate 42 by pulling up the member 43 perpendicularly to the main surface of the substrate 42. As a result, as shown in (D) of FIG. 4, an organic semiconductor film 5 which is formed of crystals of the specific compound and has good film quality can be formed without leaving a trace of the member 43 on the crystals of the specific compound.

From the viewpoint of film quality, and viewpoint that a mechanism for holding the member 43 is unnecessary and the distance (contact state) of the member 43 to the substrate 42 can be maintained, the method of applying the coating liquid in a state in which the substrate 42 and the member 43 are in contact with each other is preferable to the method of applying the coating liquid in a state in which the distance between the substrate 42 and the member 43 is kept constant.

Figure 5:
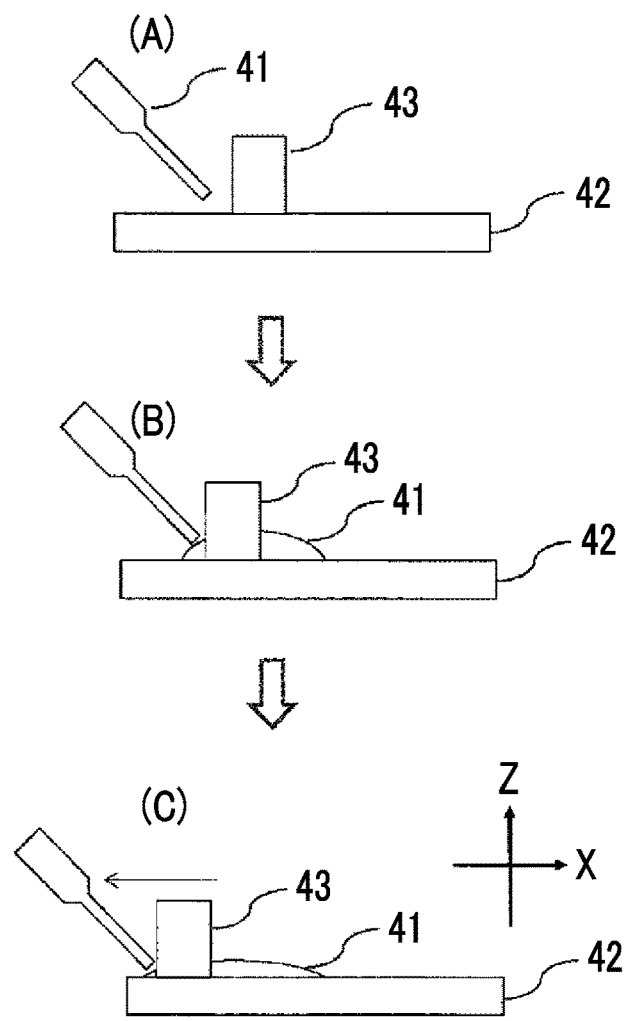
FIG. 5 is a schematic view showing still another example of the method of forming an organic semiconductor film of the organic thin film transistor.

Hereinafter, another method of applying the coating liquid in a state in which the substrate and the member are in contact with each other in this aspect will be described with reference to FIG. 5. FIG. 5 is a schematic view showing another example of the method of forming an organic semiconductor film of the organic TFT.

This method differs from the method shown in FIG. 4 in that the crystallization of the specific compound is promoted by moving the member 43 with respect to the substrate 42 while keeping the distance between the substrate 42 and the member 43 constant.

In this method, first, the substrate 42 and the member 43 are arranged in contact with each other. Specifically, before dropping a coating liquid 41 onto the substrate 42, each of the substrate 42 and the member 43 is arranged at the position shown in (A) of FIG. 5.

Next, as shown in (B) of FIG. 5, the coating liquid 41 is dropped onto a part (near a contact portion between the substrate 42 and the member 43) of the surface of the substrate 42, to be in contact with both the substrate 42 and the member 43. In this case, as shown in (B2) of FIG. 4, it is preferable that the coating liquid 41 surrounds the contact portion between the substrate 42 and the member 43.

Thereafter, while keeping the distance between the substrate 42 and the member 43 constant, the member 43 is moved with respect to the substrate 42, and the coating liquid 41 is dried. For example, the member 43 is moved with respect to the substrate 42 in an arrow direction (X-axis negative direction) in (C) of FIG. 5. Drying of the coating liquid 41 progresses from the edge (X-axis positive direction) opposite to the moving direction of the member 43 toward the moving direction (X-axis negative direction), and the specific compound is crystallized. As a result, the specific compound can be arranged at a predetermined position as a crystal having a large size.

After the coating liquid 41 is dried, for example, the member 43 is pulled away from the substrate 42 by pulling up the member 43 perpendicularly to the main surface of the substrate 42. As a result, an organic semiconductor film which is formed of the specific compound and has good film quality can be formed without leaving a trace of the member 43 on crystals of the specific compound.

The substrate 42 used in these aspects corresponds to the substrate of the organic TFT, and a substrate on which a gate insulating film is formed is preferable.

The member 43 used in these aspects is not particularly limited, but as a material of the member 43, an inorganic material (more preferably, glass, quartz, or silicon) or plastic (more preferably, Teflon (registered trademark), polyethylene, or polypropylene) is preferable, and glass is still more preferable.

The shape of the member 43 used in these aspects is not particularly limited as long as the member 43 has a smooth surface facing the substrate 42, but a rectangular parallelepiped is preferable.

Figure 6:
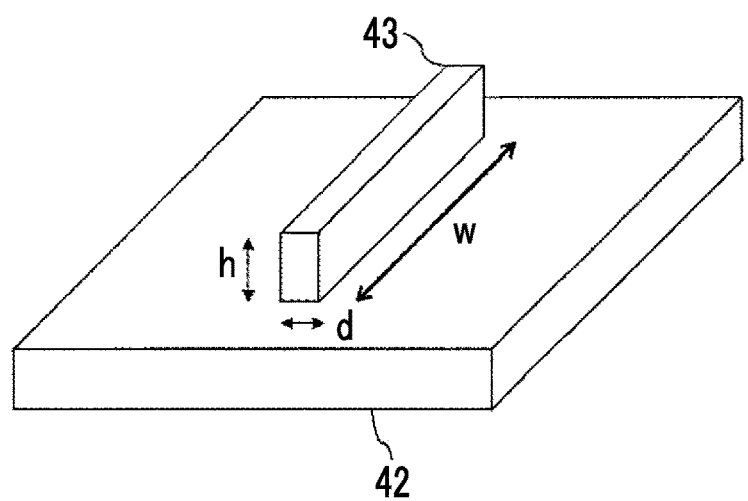
FIG. 6 is a schematic view showing an example of a substrate and a member used in the method of forming an organic semiconductor film of the organic thin film transistor.

FIG. 6 is a schematic view showing an example of the substrate 42 and the member 43 used in these aspects. In FIG. 6, the shape of the member 43 is a rectangular parallelepiped, d and w respectively represent lengths of one side and the other side of the member 43 on the surface facing the substrate 42, and h represents the height of the member 43.

The size of the member 43 used in these aspects is not particularly limited. In a case where the member 43 is a rectangular parallelepiped shown in FIG. 6, the lower limit value of the lengths (d and w in FIG. 6) of one side and the other side of the member 43 on the surface facing the substrate 42 is preferably 0.1% or more, more preferably 1% or more, still more preferably 10% or more, and particularly preferably 20% or more with respect to a length of one side of the main surface (surface on which the coating liquid is applied) of the substrate 42. In addition, the upper limit value of the above-described lengths of one side and the other side is preferably 80% or less, more preferably 70% or less, and still more preferably 50% or less with respect to the length of one side of the main surface of the substrate 42. The height (h in FIG. 6) of the member 43 is preferably 1 to 50 mm and more preferably 5 to 20 mm. Furthermore, a ratio h/d of the height h to the length d of the member 43 is preferably 0.01 to 10, and from the viewpoint of arrangement stability of the member 43, is more preferably 0.1 to 5. In addition, a ratio w/d of the length w to the length d of the member 43 is preferably 1 to 1,000, and from the viewpoint of being capable of crystallizing the specific compound in a wide range, is more preferably 5 to 100.

In this way, the crystals of the specific compound can be precipitated to form an organic semiconductor film. Whether or not the crystals of the specific compound are precipitated can be confirmed by observing the organic semiconductor film, using a polarization microscope (trade name: Eclipse LV100N POL (transmission/reflection lighting type), manufactured by Nikon Corporation, eyepiece: 10× magnification, objective lens: 5× to 20× magnification).

Use of Organic TFT

The above-described organic TFT is not particularly limited in its use, and can be used for, for example, electronic paper, display devices, sensors, and electronic tags.

Examples

Hereinafter, the present invention will be described in more detail with reference to Examples. The materials, the amounts of materials to be used, the proportions, the treatment details, and the treatment procedure shown in the examples below may be modified appropriately as long as the modifications do not depart from the spirit of the present invention. Therefore, the scope of the present invention should not be construed as being limited to the following specific examples.

Composition

Production of Composition of Example 1

The following compound (1) (1.0 mg), which is a compound for forming an organic semiconductor film and a chloroform/1,1,1,3,3,3-hexafluoro-2-propanol (HFIP) solvent (mixing ratio (volume ratio): chloroform/HFIP=4/1) were mixed to prepare a mixed solution in which the total amount was 10 g.

The mixed solution was ultrasonically irradiated at room temperature (for 15 minutes) to obtain a composition of Example 1.

Compound (1)

Production of Other Compositions

Compositions of Examples or Comparative Examples were produced in the same manner as in the procedure for producing the composition of Example 1, except that the compound for forming an organic semiconductor film and/or the type of the solvent used were changed.

The compound for forming an organic semiconductor film, which was used in the compositions of Examples 12 and 13, was a compound having the same structure as the compound for forming an organic semiconductor film, which was used in the compositions of Examples 1 to 11, but the procedure and degree of purification in a case of synthesizing the compound for forming an organic semiconductor film were different, thereby lowering the purity.

Evaluation of Solubility

The obtained composition was visually observed, and solubility of the composition was evaluated according to the following standard.

A: compound for forming an organic semiconductor film was completely dissolved in the composition.

B: undissolved residue of the compound for forming an organic semiconductor film was observed in the composition.

C: compound for forming an organic semiconductor film was not dissolved in the composition.

Evaluation of Purity by Liquid Chromatography

Using each composition, analysis was performed under the following conditions, and the area ratio of a peak derived from a target object (compound for forming an organic semiconductor film) to the total peak surface area, in a case where a detection wavelength was set as 254 nm, was calculated and evaluated according to the following standard.

A: area ratio of the target object was 99% or more.

B: area ratio of the target object was 95% or more and less than 99%.

C: area ratio of the target object was less than 95%.

D: target object was insoluble and could not be detected.

Column: using two connected Tosoh TSKgel Silica-150 (particle size: 5 μm, column size: 4.6 mm I.D.×25 cm)

Eluent: chloroform/hexafluoroisopropanol=9/1

Flow rate: 0.8 mL/min

Injection amount: 10 μL

Column temperature: 25° C.

Detection wavelength: 254 nm

Organic Thin Film Transistor

Manufacturing of Organic Thin Film Transistor

As a substrate for measuring FET characteristics, a substrate (size: 25 mm×25 mm) having a thermal oxide film (thickness: 200 nm) of $SiO_2$ on a surface of an n-type silicon substrate (thickness: 0.4 mm, corresponding to the substrate 1 provided with the gate electrode 2) 1 was prepared. A surface of the thermal oxide film (gate insulating film 3) of this substrate was washed with ultraviolet rays (UV)-ozone, and treated with β-phenethyl trimethoxysilane.

A glass member having a size of 10 mm in length×2 mm in width×5 mm in height was prepared. As the member 43 shown in FIG. 4, as shown in (A) of FIG. 4, this member was arranged at a center of the above-described substrate 1 on the β-phenethyl trimethoxysilane treated surface in a state of being contact with the treated surface.

Next, as shown in (A) of FIG. 4, using a pipette, one drop (approximately 0.05 mL) of the composition prepared by the above-described method was dropped, from a side portion of a member 43, onto the substrate 1 (represented by the reference numeral 42 in FIG. 4) at room temperature, to be in contact with the substrate 42 and the member 43 in a vicinity of the contact portion between the substrate 42 and the member 43. As shown in (B1) of FIG. 4 and (B2) of FIG. 4, the coating liquid surrounded the above-described contact portion and formed a concave meniscus at an interface with the member 43.

As shown in (C) of FIG. 4, the coating liquid 41 was dried at room temperature while maintaining the state in which the substrate 42 and the member 43 were in contact with each other and keeping the positional relationship between the substrate 42 and the member 43 stationary. Thereafter, the product was dried under a reduced pressure of $10^{-3}$ Pa at 60° C. for 8 hours to produce a crystal film of an organic semiconductor film. Next, the member 43 was pulled up perpendicularly to the substrate 42 and pulled away from the substrate 42. As a result, as shown in (D) of FIG. 4, an annular organic semiconductor film 5 having the above-described uniform film thickness (film thickness: 10 to 50 nm) was formed.

In a case where the obtained organic semiconductor film 5 was observed with a polarization microscope Eclipse LV100N POL (transmission/reflection lighting type, manufactured by Nikon Corporation, eyepiece: 10× magnification, objective lens: 5× to 20× magnification), crystals of the above-described compound (compound for forming an organic semiconductor film) were precipitated.

By placing a mask having a predetermined opening on the organic semiconductor film 5 obtained as above and vapor-depositing gold, a source electrode 4A and a drain electrode 4B (both thickness: 40 nm, gate width W=2 mm, gate length L=50 μm, ratio W/L=40) were formed. In this way, an organic thin film transistor (referred to as OTFT in each table) T for measuring FET characteristics was manufactured.

Evaluation of Organic Thin Film Transistor

With respect to each of the manufactured organic thin film transistors, carrier mobility under a normal atmospheric pressure of 1 atm (temperature: room temperature) was evaluated using a semiconductor parameter analyzer (4156C, manufactured by Agilent Technologies, Inc.) connected to a semi-auto prober (AX-2000, manufactured by Vector Semiconductor Co., Ltd.).

Evaluation of Carrier Mobility (Relative Mobility)

1. Measurement of Carrier Mobility μ after Manufacturing

A voltage of −80 V was applied between the source electrode and the drain electrode of each organic thin film transistor, the gate voltage was changed to in a range of +20 V to −100 V, and a carrier mobility μ (cm$^2$/Vs) was calculated using the following equation representing the drain current $I_d$.

$$I_d = (w/2L)\mu C_i (V_g - V_{th})^2$$

In the equation, L represents the gate length, w represents the gate width, μ represents the carrier mobility, $C_i$ represents the capacity per unit area of the gate insulating film, $V_g$ represents the gate voltage, and $V_{th}$ represents the threshold voltage, respectively.

Based on the mobility of Example 1 (mobility calculated using the organic thin film transistor manufactured using the composition of Example 1), the relative mobility was calculated by the following equation and evaluated according to the following standard.

It is preferable that the carrier mobility is high, and in the present test, the carrier mobility μ is preferably rank C or more, more preferably rank B or more, and still more preferably rank A.

Relative mobility=(Mobility of Example or Comparative Example)/(Mobility of Example 1)

A: relative mobility was 1.0 or more.
B: relative mobility was 0.5 or more and less than 1.0.
C: relative mobility was 0.1 or more and less than 0.5.
D: relative mobility was less than 0.1.

Result

The results are shown in Table 1.

In Table 1, the "Structure" column indicates which of (X), (Y), and (Z) shown below is the structure of the compound for forming an organic semiconductor film contained in the composition.

In a case where the structure of the compound for forming an organic semiconductor film is (X) or (Y), the "Group" column indicates structures of $X^1$, $X^2$, $Y^1$, and $Y^2$, which are groups included in the structure. The description of "Ph" is a phenyl group. In addition, the groups represented by "$C_5H_{11}$", "$C_8H_{17}$", and "$CH_2CH_2C_6F_{13}$" are all linear groups.

The "Solvent" column indicates the type (upper row) and volume ratio (lower row) of the solvent contained in the composition. In a case where the composition contains only one solvent, the volume ratio is not stated.

The solvent described in the "A" column of the "Solvent" column is the alcohol represented by Formula (51), and the solvent described in the "B" column is another organic solvent.

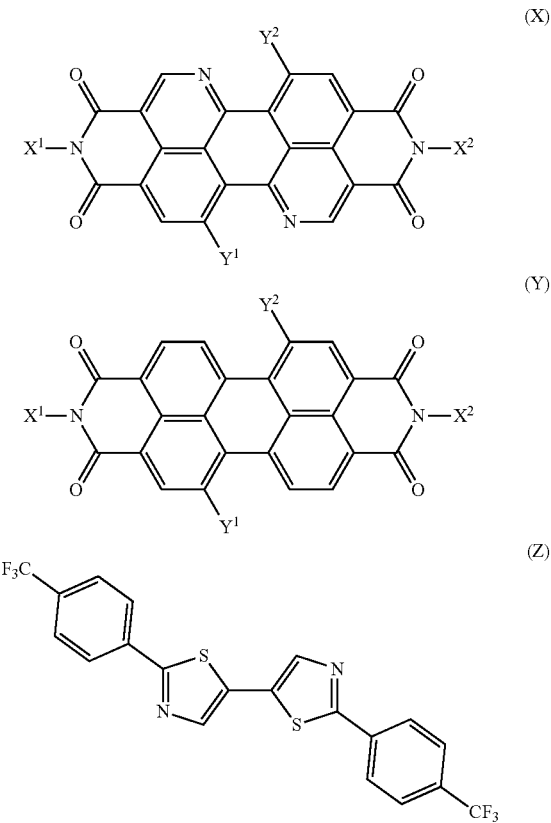

TABLE 1

| | | Compound for forming organic semiconductor film | | | | | | | | |
| | | | Group | | | | Solvent | | | Relative |
| | Structure | $X^1$ | $X^2$ | $Y^1$ | $Y^2$ | A | B | Solubility | Purity | mobility |
|---|---|---|---|---|---|---|---|---|---|---|
| Example 1 | (X) | $CH_2CH_2Ph$ | $CH_2CH_2Ph$ | H | H | HFIP | CHCl$_3$ 1:4 | A | A | A |

TABLE 1-continued

| | | Compound for forming organic semiconductor film | | | | | | | | Relative |
|---|---|---|---|---|---|---|---|---|---|---|
| | | Group | | | | Solvent | | | | |
| | Structure | $X^1$ | $X^2$ | $Y^1$ | $Y^2$ | A | B | Solubility | Purity | mobility |
| Example 2 | (X) | $CH_2CH_2Ph$ | $CH_2CH_2Ph$ | H | H | HFMP | $CHCl_3$ 1:4 | A | A | A |
| Example 3 | (X) | $CH_2CH_2Ph$ | $CH_2CH_2Ph$ | H | H | NFTB | $CHCl_3$ 1:4 | A | A | A |
| Example 4 | (X) | $CH_2CH_2Ph$ | $CH_2CH_2Ph$ | H | H | HFPP | $CHCl_3$ 1:4 | A | A | A |
| Example 5 | (X) | $CH_2CH_2Ph$ | $CH_2CH_2Ph$ | H | H | HFPP | PhCl 1:4 | A | A | A |
| Example 6 | (X) | $CH_2CH_2Ph$ | $CH_2CH_2Ph$ | H | H | HFIP | toluene 1:4 | A | A | A |
| Example 7 | (X) | $CH_2CH_2Ph$ | $CH_2CH_2Ph$ | H | H | HFPP | TCE 1:4 | A | A | A |
| Example 8 | (X) | $CH_2CH_2Ph$ | $CH_2CH_2Ph$ | H | H | HFPP | tetralin 1:4 | A | A | A |
| Example 9 | (X) | $CH_2CH_2Ph$ | $CH_2CH_2Ph$ | H | H | HFIP | THF 1:4 | B | A | B |
| Example 10 | (X) | $CH_2CH_2Ph$ | $CH_2CH_2Ph$ | H | H | HFIP | anisole 1:4 | B | A | B |
| Example 11 | (X) | $CH_2CH_2Ph$ | $CH_2CH_2Ph$ | H | H | HFIP | PhCN 1:4 | B | A | B |
| Example 12 | (X) | $CH_2CH_2Ph$ | $CH_2CH_2Ph$ | H | H | HFIP | $CHCl_3$ 1:4 | A | B | B |
| Example 13 | (X) | $CH_2CH_2Ph$ | $CH_2CH_2Ph$ | H | H | HFIP | $CHCl_3$ 1:4 | A | C | C |

TABLE 2

| | | Compound for forming organic semiconductor film | | | | | | | | Relative |
|---|---|---|---|---|---|---|---|---|---|---|
| | | Group | | | | Solvent | | | | |
| | Structure | $X^1$ | $X^2$ | $Y^1$ | $Y^2$ | A | B | Solubility | Purity | mobility |
| Example 14 | (X) | $C_8H_{17}$ | $C_8H_{17}$ | H | H | HFIP | $CHCl_3$ 1:4 | A | A | B |
| Example 15 | (X) | $C_8H_{17}$ | $C_8H_{17}$ | CN | CN | HFIP | $CHCl_3$ 1:4 | A | A | A |
| Example 16 | (X) | $C_8H_{17}$ | $C_8H_{17}$ | CN | CN | HFIP | $CHCl_3$ 1:9 | A | A | A |
| Example 17 | (X) | $C_8H_{17}$ | $C_8H_{17}$ | CN | CN | HHP | $CHCl_3$ 1:10 | B | A | B |
| Example 18 | (X) | $C_8H_{17}$ | $C_8H_{17}$ | CN | CN | HFIP | $CHCl_3$ 10:1 | A | A | A |
| Example 19 | (X) | $C_8H_{17}$ | $C_8H_{17}$ | CN | CN | HFIP | | B | A | B |
| Example 20 | (X) | $C_5H_{11}$ | $CH_2CH_2Ph$ | H | H | HFIP | $CHCl_3$ 1:4 | A | A | A |
| Example 21 | (X) | $CH_2CH_2C_6F_{13}$ | $CH_2CH_2Ph$ | H | H | HFIP | $CHCl_3$ 1:4 | A | A | B |
| Example 22 | (X) | 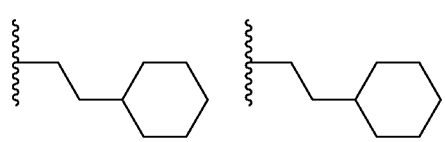 | 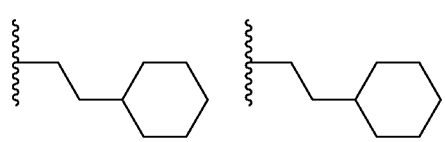 | H | H | HHP | $CHCl_3$ 1:4 | A | A | A |
| Example 23 | (Y) | $CH_2CH_2Ph$ | $CH_2CH_2Ph$ | H | H | HFIP | $CHCl_3$ 1:4 | A | A | C |
| Example 24 | (X) | $CH_2CH_2Ph$ | $CH_2CH_2Ph$ | H | H | HFIP | thiophene 1:4 | B | A | B |
| Comparative Example 1 | (X) | $CH_2CH_2Ph$ | $CH_2CH_2Ph$ | H | H | | $CHCl_3$ | C | D | D |
| Comparative Example 2 | (X) | $CH_2CH_2Ph$ | $CH_2CH_2Ph$ | H | H | | TFE | C | D | D |
| Comparative Example 3 | (X) | $CH_2CH_2Ph$ | $CH_2CH_2Ph$ | H | H | | PhCl | C | D | D |
| Comparative Example 4 | (X) | $CH_2CH_2Ph$ | $CH_2CH_2Ph$ | H | H | | Toluene | C | D | D |

TABLE 2-continued

| | | Compound for forming organic semiconductor film | | | | | | | | |
| | | Group | | | | Solvent | | | | Relative |
| | Structure | $X^1$ | $X^2$ | $Y^1$ | $Y^2$ | A | B | Solubility | Purity | mobility |
|---|---|---|---|---|---|---|---|---|---|---|
| Comparative Example 5 | (X) | $CH_2CH_2Ph$ | $CH_2CH_2Ph$ | H | H | | anisole | C | D | D |
| Comparative Example 6 | (Y) | $CH_2CH_2Ph$ | $CH_2CH_2Ph$ | H | H | | Toluene | C | D | D |
| Comparative Example 7 | (Z) | — | — | — | — | | $CHCl_3$ | A | A | D |
| Comparative Example 8 | (Z) | — | — | — | — | HFIP | $CHCl_3$ 1:4 | A | A | D |

HFIP = hexafluoroisopropanol
HFMP = 1,1,1,3,3,3-hexafluoro-2-methyl-2-propanol
NFTB = nonafluoro-tert-butanol
HFPP = 1,1,1,3,3,3-hexafluoro-2-phenyl-2-propanol
TFE = 2,2,2-trifluoroethanol
TCE = 1,1,2,2-tetrachloroethane
THF = tetrahydrofuran
PhCl = chlorobenzene
PhCN = benzonitrile From the results shown in Table 1, it was confirmed that the composition according to the embodiment of the present invention could be used to manufacture an organic thin film transistor having excellent carrier mobility even under low temperature conditions.

In addition, it was confirmed that the composition according to the embodiment of the present invention dissolved the composition for forming an organic semiconductor film well and could be analyzed by liquid chromatography, it was easy to confirm and/or adjust the purity of the composition, and it was easy to improve performance and quality of the organic thin film transistor.

From the results of Examples 19 and 18, and the like, it was confirmed that, in a case where the composition contains an organic solvent other than the alcohol represented by Formula (S1), the solubility of the composition and the carrier mobility of the obtained organic thin film transistor were more excellent.

From the comparison between Examples 16 and 17, and the like, it was confirmed that, in a case where the content of the alcohol represented by Formula (S1) to the total content of the solvent (total content of the alcohol represented by Formula (S1) and the organic solvent other than the alcohol represented by Formula (S1)) was 10% by volume or more, the solubility of the composition and the carrier mobility of the obtained organic thin film transistor were more excellent.

From the comparison between Examples 1 to 8 and Examples 9 to 11 and 24, and the like, it was confirmed that, in a case where the organic solvent other than the alcohol represented by Formula (S1) was a compound consisting of only one or more atoms selected from the group consisting of a carbon atom, a hydrogen atom, and a halogen atom, the solubility of the composition and the carrier mobility of the obtained organic thin film transistor were more excellent.

From the comparison of Examples 1, 12, and 13, and the like, it was confirmed that, in a case where the purity of the specific compound was high, the carrier mobility of the obtained organic thin film transistor was more excellent.

From the comparison of Examples 1 and 23, and the like, it was confirmed that, in a case where $B^{11}$ to $B^{18}$ with —N= were present in $B^{11}$ to $B^{18}$ in the specific compound, the carrier mobility of the obtained organic thin film transistor was more excellent.

EXPLANATION OF REFERENCES

1: substrate
2: gate electrode
3: gate insulating film
4A: source electrode
4B: drain electrode
5: organic semiconductor film (organic semiconductor layer)
6: sealing layer
10, 20: organic thin film transistor (organic TFT)
41: coating liquid
42: substrate
43: member

What is claimed is:
1. A composition comprising:
a compound represented by Formula (1); and
an alcohol represented by Formula (S1),

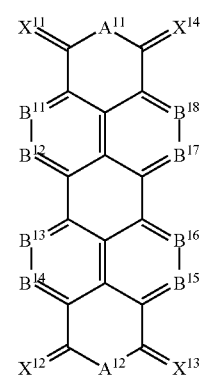

(1)

in Formula (1),
$A^{11}$ and $A^{12}$ each independently represent —O—, —N($R^N$)—, or —P($R^N$)—,
$B^{11}$ to $B^{18}$ each independently represent —N= or —C($R^M$)=,
at least one of $B^{11}$, $B^{12}$, $B^{13}$, $B^{14}$, $B^{15}$, $B^{16}$, $B^{17}$, or $B^{18}$ is —N=, $R^N$ and $R^M$ each independently represent a hydrogen atom or a substituent, and $X^{11}$ to $X^{14}$ each independently represent an oxygen atom or a sulfur atom,

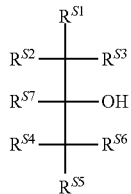

(S1)

in Formula (S1), $R^{S1}$ to $R^{S6}$ each independently represent a hydrogen atom, a fluorine atom, or a substituent, $R^{S7}$ represents a hydrogen atom or a substituent, and at least four of $R^{S1}$ to $R^{S6}$ are fluorine atoms.

2. The composition according to claim 1, further comprising:

an organic solvent other than the alcohol represented by Formula (S1).

3. The composition according to claim 2, wherein the organic solvent consists of only one or more atoms selected from the group consisting of a carbon atom, a hydrogen atom, and a halogen atom.

4. The composition according to claim 2, wherein, in the composition, a content of the alcohol represented by Formula (S1) is 10% by volume or more with respect to a total content of the alcohol represented by Formula (S1) and the organic solvent.

5. The composition according to claim 2, wherein the alcohol represented by Formula (S1) in the composition is an alcohol represented by Formula (S2),

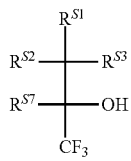

(S2)

in Formula (S2), $R^{S1}$ to $R^{S3}$ each independently represent a hydrogen atom, a fluorine atom, or a substituent, $R^{S7}$ represents a hydrogen atom or a substituent, and at least one of $R^{S1}$, $R^{S2}$, or $R^{S3}$ is a fluorine atom.

6. The composition according to claim 2, wherein the alcohol represented by Formula (S1) in the composition is an alcohol represented by Formula (S3),

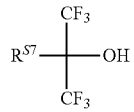

(S3)

in Formula (S3), $R^{S7}$ represents a hydrogen atom or a substituent.

7. The composition according to claim 2, wherein the composition is a composition for forming an organic semiconductor layer.

8. The composition according to claim 2, wherein the composition is a composition for forming an organic semiconductor layer for an organic thin film transistor.

9. The composition according to claim 1, wherein the alcohol represented by Formula (S1) in the composition is an alcohol represented by Formula (S2),

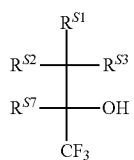

(S2)

in Formula (S2), $R^{S1}$ to $R^{S3}$ each independently represent a hydrogen atom, a fluorine atom, or a substituent, $R^{S7}$ represents a hydrogen atom or a substituent, and at least one of $R^{S1}$, $R^{S2}$, or $R^{S3}$ is a fluorine atom.

10. The composition according to claim 1, wherein the alcohol represented by Formula (S1) in the composition is an alcohol represented by Formula (S3),

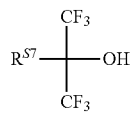

(S3)

in Formula (S3), $R^{S7}$ represents a hydrogen atom or a substituent.

11. The composition according to claim 1, wherein the composition is a composition for forming an organic semiconductor layer.

12. The composition according to claim 1, wherein the composition is a composition for forming an organic semiconductor layer for an organic thin film transistor.

* * * * *